(12) United States Patent
Nakazato

(10) Patent No.: US 8,129,978 B2
(45) Date of Patent: Mar. 6, 2012

(54) MATERIAL DETECTOR

(75) Inventor: Kazuo Nakazato, Nagoya (JP)

(73) Assignee: National University Corporation Nagoya University, Nagoya-Shi, Aichi (JP)

( * ) Notice: Subject to any disclaimer, the term of this patent is extended or adjusted under 35 U.S.C. 154(b) by 357 days.

(21) Appl. No.: 12/308,769

(22) PCT Filed: Jul. 11, 2007

(86) PCT No.: PCT/JP2007/063847
§ 371 (c)(1),
(2), (4) Date: Jun. 16, 2009

(87) PCT Pub. No.: WO2008/007716
PCT Pub. Date: Jan. 17, 2008

(65) Prior Publication Data
US 2010/0007326 A1 Jan. 14, 2010

(30) Foreign Application Priority Data
Jul. 13, 2006 (JP) .................................. 2006-193425

(51) Int. Cl.
*G01N 27/00* (2006.01)
*G01N 27/60* (2006.01)
*G01N 27/62* (2006.01)
(52) U.S. Cl. .................. 324/71.5; 324/452; 324/459
(58) Field of Classification Search ................. 324/71.1, 324/76.11, 452, 457, 459, 467, 71.5; 257/253
See application file for complete search history.

(56) References Cited

U.S. PATENT DOCUMENTS

| 4,657,658 | A | | 4/1987 | Sibbald | |
|---|---|---|---|---|---|
| 5,387,328 | A | * | 2/1995 | Sohn | 257/253 |
| 7,368,917 | B2 | * | 5/2008 | Chung et al. | 324/459 |
| 2008/0061323 | A1 | * | 3/2008 | Yazawa et al. | 257/253 |
| 2008/0265985 | A1 | * | 10/2008 | Toumazou et al. | 327/566 |

FOREIGN PATENT DOCUMENTS

| JP | 61-118652 | 6/1986 |
|---|---|---|
| JP | 7-74793 | 8/1995 |
| JP | 2641104 | 5/1997 |
| JP | 2001-525921 | 12/2001 |
| JP | 2003-4697 | 1/2003 |
| JP | 2004-309462 | 11/2004 |
| JP | 2005-207797 | 8/2005 |
| JP | 2006-503279 | 1/2006 |
| WO | WO98/01758 | 1/1998 |
| WO | WO2004/036203 | 4/2004 |

OTHER PUBLICATIONS

Bergveld, P., "Thirty years of ISFETOLOGY: What happened in the past 30 years and what may happen in the next 30 years," Sensors and Actuators B 88(2003)pp. 1-20, 2002.

* cited by examiner

*Primary Examiner* — Hoai-An D Nguyen
(74) *Attorney, Agent, or Firm* — McGinn IP Law Group, PLLC

(57) ABSTRACT

To realize a small size and high detection accuracy in a substance detection apparatus. A charge detection field effect transistor and a control circuit therefor are provided in each cell, and the control circuit controls the charge detection field effect transistor so that the drain-source voltage and the drain current of the charge detection field effect transistor are always maintained constant. The control circuit may be formed in a CMOS configuration including a small number of elements in a small area using a standard CMOS integrated circuit technique.

36 Claims, 31 Drawing Sheets

(a)

(b)

MATERIAL DETECTOR

TECHNICAL FIELD

The present invention relates to a substance detection apparatus configured to detect DNA, a biocell group, a biomolecule, a bio substance, or other substances having a charge, or a charge distribution, a change in charge, a phenomenon with a change in capacitance. Particularly, the present invention relates to a CMOS biochip realized by disposing charge detection transistors in the form of a matrix array and integrating the matrix array of charge detection transistors together with control circuits on a single chip. More particularly, the present invention relates to a DNA chip of a substance detection apparatus configured to electrically identify a base sequence of DNA.

BACKGROUND ART

A charge detection transistor shown in FIG. 1 is used as an ISFET (ion sensitive field effect transistor) to detect an ion charge in a solution. This transistor is basically similar to a MOSFET (Metal-Oxide-Semiconductor Field Effect Transistor) except that it does not have a gate electrode, and a gate insulating film is in direct contact with a solution. A more detailed description of the ISFET may be found, for example, in Non-Patent Document 1 in a list shown below.

A source region 2 and a drain region 3 of a high-density N-type diffusion layer are formed in a P-type silicon substrate 1, and a gate insulating film 4 is formed on a surface of the substrate. The gate insulating film 4 is in-contact with a solution 5 in which a reference electrode 6 is disposed. A bias is set such that an inversion layer 7 is formed on a Si surface between the source 2 and the drain 3 thereby to detect an ion charge in the solution from a current flowing through the inversion layer. Normally, the ISFET is operated with a constant current. In this case, a potential difference between the reference electrode 6 and the source 2 is detected. To detect the presence of a particular ion, the potential difference is measured between a solution in which there is no ion and a solution including the ion. However, the potential difference caused by the ion charge is as small as a few tens of millivolts, and thus a special concern is needed in detection thereof.

An example of a conventional ISFET control circuit is shown in FIG. 2. The threshold value of the ISFET varies due to variations in production conditions. However, required resolution is smaller than the variation width in threshold value of as-produced ISFETs. Therefore, to achieve required resolution, gate potential differences are sequentially stored, and measured values are compared before and after measurement. In this method, it is more important to minimize the variation in transistor characteristics and minimize degradation of gate insulation films after production than to minimize the variations that occur during production.

In FIG. 2, the reference electrode is always grounded. A current from a direct-current power source Uref flows through a path including a direct-current connection path passing through a resistor R0, a node N1, and R02 and a direct-current connection path passing though a resistor R03, a node N2, and the ISFET. Potentials of the nodes N1 and N2 are adjusted by an operational amplifier such that the node N1 and the node N2 are at the same potential. As a result, a constant drain current R01Uref/R03(R01+R02) flows through the ISFET, the voltage between the drain and source is maintained at a constant value R02 Uref/(R01+R02), and Uout is determined such that the above-described operating point of the transistor is achieved. The ISFET is used as a source follower thereby to achieve a great detection range. The ISFET is always kept in an ON state so that even if an abnormal charge appears in a solution, such an abnormal charge is compensated for by movement of carries in an inversion layer thereby preventing the gate insulating film from being easily degraded. Furthermore, the drain-to-source voltage is always kept at a relatively low value (for example, 0.5 volts). This prevents hot electrons from being generated and thus prevents the gate insulating film from being degraded and preventing surface states from being created. Diodes D1 and D2 are connected in parallel to Uout whereby the source voltage of the ISFET is always kept at a voltage in the range of −1.3 V to 3 V thereby protecting the ISFET.

Patent Document 1 in a list shown below discloses a technique in which a differential amplifier is formed with a charge detection transistor and a reference transistor such that a difference signal indicating a difference between a state in which there is a substance on a gate and a state in which there is no substance is output thereby achieving an improvement in detection accuracy.

Patent Document 2 in the list shown below discloses a circuit in which a charge detection transistor and a reference transistor are inserted in a path on the drain side of a current mirror circuit so that drain outputs thereof are differentially amplified. Also in this technique, as is in the technique disclosed in Patent Document 1, a difference signal indicating a difference between a state in which there is a substance on a gate and a state in which there is no substance is output thereby achieving an improvement in detection accuracy.

Patent Document 3 discloses a circuit in which a sample measurement electrode connected to a gate electrode of a charge detection transistor is charged, and a substance on the measurement electrode is detected by capacitive voltage division. Patent Document 3 also discloses a technique in which after the gate electrode of the charge detection transistor is charged, the gate is cut off, an attenuation characteristic of a reduction in the gate voltage is measured, and a substance is detected based on an attenuation constant thereof.

Patent Document 5 discloses a technique in which a pressure is measured by detecting a change in a drain voltage that occurs when the pressure is applied while maintaining a gate voltage and a drain current at constant values.

Patent Document 6 discloses a sensor configured to detect a chemical substance on a detection FET by a differential output between the detection FET and a non-detection FET.

Patent Document 7 discloses an apparatus configured to determine the quantity of nucleic acid using elements having various detection areas. In any technique disclosed in Documents cited above, differential amplification is used.

Non-Patent Document 1: P. Bergveld, "Thirty years of ISFE-TOLOGY What happened in the past 30 years and what may happen in the next 30 years," Sensors and Actuators B 88 (2003) pp. 1-20

Patent Document 1: Japanese Examined Patent Application Publication No. 7-74793

Patent Document 2: Japanese Unexamined Patent Application Publication No. 2005-207797

Patent Document 3: Japanese Unexamined Patent Application Publication No. 2003-4697

Patent Document 4: PCT Japanese Translation Patent Application Publication No. 2006-503279

Patent Document 5: Japanese Unexamined Patent Application Publication No. 2-184728

Patent Document 6: Japanese Unexamined Patent Application Publication No. 61-118652

Patent Document 7: Japanese Unexamined Patent Application Publication No. 2004-309462

DISCLOSURE OF INVENTION

Problems to be Solved by the Invention

FIG. 2 illustrates a circuit configured, for use in an apparatus, by connecting discrete components including one ISFET, one operational amplifier, three resistors, two diodes, and one battery. However, in a case where ISFETs are disposed in a 16×16 matrix array and an entire circuit including control circuits is integrated on a single chip, the circuit configuration shown in FIG. 2 is not very effective. The control circuit is for protecting the ISFET. One control circuit is needed for each ISFET. However, an operational amplifier occupies a large area, and it is not practical to dispose one operational amplifier for each of the 16×16 cells. Furthermore, a high-gain circuit such as an operational amplifier can cause oscillation or noise. In this respect, it is desirable that cells do not include an operational amplifier disposed therein. Furthermore, the direct-current power source Uref floats from the ground level, and it is difficult to produce such a power source.

A device in which charge detection transistors are disposed in a matrix array will find a wide variety of applications such as a DNA chip. Using a charge detection transistor array, it is possible to realize super-parallel high-throughput DNA sequencing and a small-sized portable medical diagnostic apparatus. It is a most important issue in the frontier of medical care to develop diagnostic technology applicable to bedside diagnosis or home medical care. In recent years, speed-up of distribution has been achieved for a wide variety of products such as foods and in many fields. However, this can cause an infectious disease to diffuse explosively without remaining in a limited local area as was in the old days, and a great number of patients can appear. To prevent such infection, a quick action is necessary. In particular, a diagnostic technique is necessary to quickly identify a large number of infected people. One of devices that make it possible to realize such a diagnostic technique is a DNA chip, as discussed below. In the DNA chip, a plurality of pieces of probe DNA having known base sequences are fixed to a matrix array. This DNA chip is then soaked in a solution of target DNA to be examined. DNA forms a double helix with DNA having a complementary base sequence. Therefore, it is possible to identify the base sequence of the target DNA based on whether a double helix is formed or not.

A common method includes applying a phosphor to the target DNA, bringing the target DNA into contact with the probe DNA, thereafter cleaning the chip and detecting whether there is a phosphor remains on the chip. In this method, it takes a long time to perform the process including applying the phosphor to the target DNA, detecting the remaining phosphor, etc. Another disadvantage is in that a large-size apparatus including an optical system is needed.

In contrast, the method using the charge detection transistor has the advantage that the operation can be automated, and the apparatus can be realized in a small form. However, a detection voltage is very low, and thus it is needed to provide a control circuit in each cell. To this end, it is necessary to realize the control circuit using common semiconductor elements within a very small size. In order to identify the base sequence of the target DNA, it is desirable that the target DNA is brought at a time into contact with a large number of probe DNA with different base sequences. To meet this requirement, it is necessary to dispose one to ten million cells on a single chip. The cost of a semiconductor chip depends on the chip size, and thus it is needed to reduce the cell size to achieve a small chip size thereby achieving a reduction in cost.

The techniques disclosed in the documents cited above are basically based on the differential amplification and have the disadvantages described above.

In view of the problems described above, it is an object of the present invention to realize a small-size apparatus capable of detecting a wide variety of substances or substances distributed in a plane.

Another object of the invention is to improve detection accuracy.

Still another object of the invention is to realize a detection apparatus capable of identifying unknown DNA structures at a time.

Still another object of the invention is to realize a CMOS biochip in a small form.

Means for Solving the Problems

According to a first aspect of the present invention, to achieve the above objects, there is provided a substance detection apparatus configured to identify a substance by measuring an amount of charge of the substance in contact with a gate of a charge detection field effect transistor, comprising cells arranged in the form of a matrix array, each cell including a charge detection field effect transistor, and a control circuit including a CMOS current mirror circuit configured to control the charge detection field effect transistor such that a current flowing through the charge detection field effect transistor and a voltage across it are maintained constant.

In this first aspect of the present invention, the control circuit configured using the CMOS circuit is disposed in each of the cells arranged in the form of the matrix array thereby to control the charge detection field effect transistor in each cell such that the voltage across the charge detection field effect transistor and the current flowing through the transistor are maintained constant. As for the charge detection transistor, a transistor known as an ion-sensitive field effect transistor (ISFET) may be used. Note that any type of transistor may be used as long as the resistance of the channel changes in response to a change in gate voltage caused by a charge of a substance in contact with the gate. A field effect transistor such as a MOSFET, a MISFET, a HEMT, a MESFET, or the like may be employed. The gate electrode may or may not be provided. As will be described later, when a charge detection field effect transistor having a gate electrode is used, it is possible to control the transistors in the cells such that the transistors have the same initial operating point that allows high sensitivity or good linearity, whereby it becomes possible to achieve high-accuracy detection. The substance detection apparatus according to the present is useful, in particular, as a CMOS biochip.

According to a second aspect based on the first aspect of the present invention, the control circuit includes a first current mirror circuit using PMOSFETs, a second current mirror circuit using NMOSFETs, and a current source, the first current mirror circuit and the second current mirror circuit being connected in series, the current source being adapted to supply a constant current to the series connection of the current mirror circuits, the charge detection field effect transistor being inserted in one of current paths, at least one selected from the group consisting of a first resistor, a first transistor and a first diode being inserted in the other one of the current paths.

In this second aspect of the invention, the control circuit is configured using the current mirror circuit of PMOSFETs and NMOSFETs such that the charge detection transistor is disposed in one of the two current paths and the first resistor or the first transistor or the first diode is disposed at a symmetrical location in the other one of the two current paths. The series connection of PMOSFETs and NMOSFETs is configured in the form of a CMOS circuit. The first resistor functioning as a load resistor of the circuit may be implemented by a resistor, a transistor, or a diode. When the load resistor is implemented by a transistor or a diode, it is possible to reduce the cell size. In particular, when a huge number of cells such as one million cells are integrated, use of a transistor or a diode as the load resistor is very effective to reduce the cell size.

According to a third aspect based on the second aspect of the present invention, the first current mirror circuit includes cascode-connected PMOSFETs, and the second current mirror circuit includes cascode-connected NMOSFETs. The cascode-connected circuit refers to a circuit configured by connecting the source of a transistor and the drain of another transistor in each current path so that a common current flows through both transistors in each current path. Gates of transistors located at symmetric positions in the respective current paths are connected to the same voltage. In general, the charge detection transistor is inserted in the source side. Depending on the polarity of a power supply used, PMOSFETs and NMOSFETs are properly disposed.

According to a fourth aspect based on the third aspect of the present invention, the first current mirror circuit and the second current mirror circuit are connected to each other via at least one selected from the group consisting of a second resistor, a second transistor and a second diode, and at least one selected from the group consisting of a third resistor, a third transistor and a third diode, inserted in respective current paths.

A lower-voltage terminal of two terminals of the second resistor or the third resistor, or the second transistor or the third transistor, or the second diode or the third diode is, respectively, connected to the gates of the cascode-connected PMOSFETs, while a higher-voltage terminal of two terminals of the third resistor or the second resistor, or the third transistor or the second transistor, or the third diode or the second diode is, respectively, connected to the gates of the NMOSFETs. By these resistors or the transistors or the diodes, the cascode-connected transistors are biased.

According to a fifth aspect based on one of the first to fourth aspects of the present invention, the current source is a circuit configured in the form of a current mirror circuit including a fourth resistor or a fourth transistor or a fourth diode functioning as a load thereby to supply a constant current.

According to a sixth aspect based on the fifth aspect of the present invention, the first resistor, the second resistor, the third resistor, and the fourth resistor, or the first transistor, the second transistor, the third transistor, and the fourth transistor, or the first diode, the second diode, the third diode, and the fourth diode are formed of the same material. This allows the resistors, the transistors, and the diodes to have the same temperature coefficients, and thus it becomes possible to suppress the temperature-dependent changes of characteristics.

According to a seventh aspect based on one of the first to sixth aspects of the present invention, each cell includes a reference field effect transistor and a reference control circuit, the reference field effect transistor having the same structure as that of the charge detection field effect transistor, the reference control circuit being adapted to supply a current to the reference field effect transistor, the reference control circuit having the same configuration as that of the control circuit adapted to control the charge detection field effect transistor, and each cell includes a first differential amplifier adapted to input an output signal depending on an operating state of the charge detection field effect transistor and an output signal depending on an operating state of the reference field effect transistor and amplifies the difference between the two output signals.

It is desirable that the charge detection field effect transistor and the reference field effect transistor have the same characteristics. To achieve the same characteristics, the transistors are generally formed to have the same size. However, there may be a difference in size, if the same characteristics are achieved. The output signals may be supplied from any point as long as the output signals change depending on the operating states, i.e., the gate voltages, of the charge detection field effect transistor and the reference field effect transistor. For example, in the case where the output signals are output via source followers, the voltages at the source terminals of the charge detection field effect transistor and the reference field effect transistor are employed as the output signals. Conversely, in the case where the output signals are output via drain followers, the voltages at the drain terminals of the charge detection field effect transistor and the reference field effect transistor may be employed as the output signals. Note that as long as it is possible to output voltages corresponding to the gate voltages of the transistors, the source terminals or the drain terminals of the transistors may be employed, or a terminal potential of the first resistor or the first transistor or the first diode located at a symmetrical position to the charge detection field effect transistor or the reference field effect transistor may be employed as the output signal.

According to an eighth aspect based on one of the first to sixth aspects of the present invention, the substance detection apparatus comprises reference field effect transistors and reference control circuits provided for respective rows of the matrix array of cells, the reference field effect transistors and the reference control circuits being disposed in a peripheral part of an area in which the matrix array of cells is disposed, the reference field effect transistors having the same structure as that of the charge detection field effect transistors, the reference control circuits being adapted to supply currents to the corresponding reference field effect transistors, the reference control circuits having the same configuration as that of the control circuit adapted to control the charge detection field effect transistors, and second differential amplifiers provided for the respective rows and each adapted to input an output signal depending on an operating state of the corresponding charge detection field effect transistor and an output signal depending on an operating state of the corresponding reference field effect transistor and amplifies the difference between the two output signals.

The only one set of the reference field effect transistors and the reference control circuits may be provided for all cells in common. If the rectangular shape of the matrix array of cells is taken into account, it is desirable in design to provide reference field effect transistors and reference control circuits in units of rows. Note that the row refers to a sequence of cells arranged along one of x and y axes of the matrix array. The output signal is similar to that in the seventh aspect described above.

According to a ninth aspect based on one of the first to sixth aspects of the present invention, each cell includes an output transistor with a gate connected to the source of the charge detection field effect transistor, a pass gate transistor connected to the source of the output transistor and adapted to pass or cut off the output of the output transistor depending on an external selection signal thereby outputting the output signal to the outside of the cell, and a signal line adapted to transmit the output signal from the pass gate transistor to a peripheral part of the area of the matrix array of cells.

The selection signal may make selection in units of rows or columns or may identity a particular cell in a selected row and a selected column.

According to a tenth aspect based on the ninth aspect of the present invention, the substance detection apparatus comprises a third differential amplifier disposed in a peripheral part of the area of the matrix array of cells and adapted to input the output signal from the signal line to one input terminal of the third differential amplifier, a resistor or a transistor connected between two input terminals of the third differential amplifier, a feedback line connecting the other input terminal of the third differential amplifier to each cell, and a feedback transistor provided in each cell and adapted to pass or cut off a signal depending on the selection signal thereby feeding back the fed-back output signal to a common potential via the feedback line.

The selection signal is similar to that in the ninth aspect of the invention. Therefore, if the selection signal is used to perform row selection, the third differential amplifiers are provided in units or columns. In this case, as many third differential amplifiers are provided as there are columns. Conversely, in the case where the selection signal is used to perform column selection, the third differential amplifiers are provided in units or rows. In this case, as many third differential amplifiers are provided as there are rows.

In the case where the selection signal performs selection in units of cells, as many third differential amplifiers are provided as there are cells. Note that the concept of the third differential amplifier includes an operational amplifier. The second differential amplifiers are disposed in a similar manner to the third differential amplifiers.

According to an eleventh aspect based on one of the first to tenth aspects of the present invention, each charge detection field effect transistor has a gate electrode on an insulating film.

According to a twelfth aspect based on the eleventh aspect of the present invention, the substance detection apparatus comprises a charging transistor adapted to supply or cut off a bias voltage to the gate electrode. The charging transistor provided is for setting the initial operating point of the charge detection field effect transistor. When a measurement is performed, the charging transistor is turned off. To avoid an influence on the measurement, it is desirable that a leakage current of the charging transistor be as small as possible. In practice, it is sufficient if the leakage current is so small that it can be neglected during a measurement period. To reduce the leakage current, it is desirable that the voltage of the charging bias source is applied to the transistor even during a period in which the charging transistor is in the off state.

According to a thirteenth aspect based on the seventh aspect of the present invention, the reference field effect transistor in each cell has a gate electrode on an insulating film, each cell includes a first charging transistor adapted to supply or cut off a bias voltage to the gate electrode according to an external charge control signal, the charge detection field effect transistor in each cell has a gate electrode on an insulating film, and each cell includes a fourth differential amplifier and a second charging transistor, the fourth differential amplifier being adapted to input an output signal depending on an operating state of the corresponding charge detection field effect transistor and an output signal depending on an operating state of the corresponding reference field effect transistor and amplifies the difference between the two output signals, the second charging transistor being a transistor adapted to supply or cut off a bias voltage in accordance with the charge control signal so as to apply the output of the fourth differential amplifier to the gate electrode of the charge detection field effect transistor.

The output signal is similar to that in the seventh aspect described above. In this aspect, the reference field effect transistor having the gate electrode and the reference control circuit are disposed in each cell. The substance detection is performed using the difference signal, and thus it is possible to achieve high detection accuracy.

According to a fourteenth aspect based on the eighth aspect of the present invention, each reference field effect transistor has a gate electrode on an insulating film, a first charging transistor is provided for supplying or cutting off a bias voltage to the gate electrode according to an external charge control signal, the charge detection field effect transistor in each cell has a gate electrode on an insulating film, and a second charging transistor is provided for applying, to the gate electrode of the charge detection field effect transistor, an amplified difference voltage between an output signal depending on an operating state of the charge detection field effect transistor and an output signal depending on an operating state of the reference field effect transistor thereby supplying or cutting off a bias voltage according to the charge control signal.

The output signal is similar to that in the seventh aspect described above. By providing the reference field effect transistors and the reference control circuits in units of rows, it becomes possible to reduce the total apparatus size and simplify the structure of the apparatus.

According to a fifteenth aspect based on one of the eleventh to fourteenth aspects of the present invention, the gate electrode of the charge detection field effect transistor is an extension gate electrode extending immediately over the charge detection field effect transistor and the control circuit.

That is, the gate electrode is formed so as to extend to an area immediately above the control circuit thereby reducing the size.

According to a sixteenth aspect of the present invention, the extension of the gate electrode according to the fifteenth aspect of the invention is also applied to the reference field effect transistor.

According to a seventeenth aspect based on one of the first to sixteenth aspects of the invention, a power supply voltage supplied to each cell is within the range of 3 V to −1.3 V.

According to an eighteenth aspect based on one of the first to seventeenth aspects of the invention, a word line adapted to select one row of the matrix array of cells and a bit line adapted to transmit a signal from a cell in each column.

According to a nineteenth aspect based on the thirteenth or fourteenth aspect of the invention, the substance detection apparatus comprises a fifth transistor and a sixth transistor adapted to apply voltages corresponding to voltages of gate electrodes of the reference field effect transistor and the charge detection field effect transistor to terminals, which are not connected to the gates of the reference field effect transistor and the charge detection field effect transistor, of the first charging transistor and the second charging transistor when the first charging transistor and the second charging transistor are in OFF states so that the source-drain voltage becomes zero for these first charging transistor and second charging transistor in the OFF states.

According to a twentieth aspect based on the thirteenth, fourteenth, or nineteenth aspect of the invention, there are provided a seventh transistor and an eighth transistor, the seventh transistor being disposed between the gate electrode of the reference field effect transistor and the fifth transistor, the seventh transistor being adapted to absorb a charge of a channel of the first charging transistor when the first charging transistor is in an OFF state, the eighth transistor being disposed between the gate electrode of the charge detection field effect transistor and the second charging transistor, the eighth transistor being adapted to absorb a charge of a channel of the second charging transistor when the second charging transistor is in an OFF state.

According to a twenty first aspect based on one of the first to twentieth aspects of the invention, the substance detection apparatus comprises a second output circuit adapted to output, as an output signal, a gate voltage of the charge detection field effect transistor.

According to a twenty second aspect based on one of the seventh, eighth, and thirteenth to twenty first aspects of the invention, the substance detection apparatus comprises a first output circuit adapted to output, as an output signal, a gate voltage of the reference field effect transistor.

According to a twenty third aspect based on the twenty first aspect of the present invention, the substance detection apparatus comprises a second startup circuit adapted to be maintained in the operating state, i.e., to suppress an increase in output impedance of the second output circuit, when the gate voltage of the charge detection field effect transistor is low.

According to a twenty fourth aspect based on the twenty second aspect of the invention, the substance detection apparatus comprises a first startup circuit adapted to be maintained in the operating state, i.e., to suppress an increase in output impedance of the first output circuit, when the gate voltage of the reference field effect transistor is low.

According to a twenty fifth aspect based on one of the first to twenty fourth aspects of the invention, the substance detection apparatus comprises a bias circuit adapted to supply a bias voltage to a transistor in each cell, the bias circuit including a current mirror circuit adapted to control currents such that a reference current flowing through a charge detection transistor is equal for adjacent cells, the bias circuit also including a current mirror circuit adapted to control currents such that the reference current is equal to a reference current that is input to the current mirror circuit.

According to a twenty sixth aspect based on the twenty fifth aspect of the invention, there is provided a substance detection apparatus in which the reference current is controlled to have a large value for a cell being measured and to have a small value for a cell being not measured.

According to a twenty seventh aspect based on the first to twenty sixth aspects of the invention, the substance detection apparatus is an apparatus adapted to detect one of DNA, a biomolecule, a biocell group, and a bio substance.

Advantages

In the first and second aspects of the invention, the control circuit of each cell is configured using a current mirror circuit in the form of a CMOS configuration.

In this configuration, using the control circuit occupying a small area in each cell, it is possible to protect the charge detection field effect transistor in each cell.

By disposing cells in the form of a matrix array, it is possible to detect a large number of substances at a time.

In the case of a substance having a planar charge distribution, it is possible to detect the planar distribution of the substance. Furthermore, by combining NMOSFETs and PMOSFETs, it is possible to realize a circuit with a less number of components capable of operating with less consumption power.

In the third aspect of the invention, the first current mirror circuit and the second current mirror circuit are realized by cascode-connected MOSFETs. This allows a reduction in the channel length modulation effect that occurs in MOSFETs with a short channel length. Therefore, it is possible to achieve high accuracy when the size is reduced by using MOSFETs with a small channel length.

In the fourth aspect of the invention, transistors associated with the current mirror control are self-biased using a resistor, a transistor, or a diode without using a bias circuit. This allows simplification of the circuit configuration.

In the fifth aspect of the invention, a constant current is supplied to the current mirror circuit. In the sixth aspect of the invention, the resistors, the transistors, or the diodes are formed using the same material. This eliminates the effects of a temperature variation on the resistors, the transistors, or the diodes.

In the seventh aspect of the invention, the reference field effect transistor whose gate is not brought into contact with a substance to be detected is provided in each cell, and the detection signal relative to the background reference signal is output. Thus, it is possible to achieve high-accuracy detection. In the eighth aspect of the invention, the reference field effect transistor and the control circuit thereof are provided in units of rows of the matrix array of cells. This allows a reduction in the circuit size.

In the ninth aspect of the invention, the signal detected in each cell can be output. In the tenth aspect of the invention, the signal output in units of rows of the matrix array of cells is fed back to each cell. This allows a reduction in influence of noise, and thus it is possible to improve the detection accuracy.

In the eleventh aspect of the invention, the gate electrode is provided on the gate insulating film of the charge detection field effect transistor. This protects the gate and it becomes possible to easily fix DNA or a biomolecule by a self-assembled monolayer film. In the twelfth aspect of the invention, the initial operating point of the charge detection field effect transistor in each cell can be set in an optimum region. In the thirteenth aspect of the invention, the reference field effect transistor is configured to have the gate electrode, and a voltage is applied to the gate electrode of the charge detection field effect transistor so that the output terminal voltage of the charge detection field effect transistor is equal to the output terminal voltage of the reference field effect transistor. This leads to simplification of the circuit, and it becomes possible to start the operation in a state in which the charge detection transistor and the reference transistor are at the same initial operating point.

In the fourteenth aspect of the invention, the reference field effect transistor and the control circuit thereof are provided in units of rows of the matrix array of cells. This makes it possible to reduce the circuit size and simplify the circuit configuration.

In the fifteenth aspect and the sixteenth aspect of the invention, the gate electrode is formed so as to extend to a point immediately above the control circuit. This makes it possible to separate the gate unit from the transistor unit. Thus, it is possible to form the detection apparatus such that only the gate unit that is subjected to a reaction is disposable, and the transistor unit can be used repeatedly. Thus, it is possible to develop an economical measurement technique. Besides, it is possible to achieve a circuit with a high integration density.

In the seventeenth aspect of the invention, the voltage range of the electrode is limited so that an electrolytic reaction between the electrode and a solution is prevented, thereby achieving stable operation. In the eighteenth aspect of the invention, signals of cells in the matrix array are output in units of rows, and thus it is possible to simplify the circuit configuration.

In the nineteenth aspect of the invention, when the charging transistor is turned off after charging of the gate electrodes of the charge detection transistor and the reference transistor is completed, the voltage is applied so that drain-source voltage becomes zero and thus a leakage current from the gate electrode can be prevented. Thus, it is possible to improve the detection accuracy.

In the twentieth aspect of the invention, the amount of carriers stored on the gate electrode can be controlled with high accuracy, and thus it is possible to improve the measurement accuracy.

In the twenty first and twenty second aspect of the invention, the output signal is given by the gate voltage of the charge detection transistor and that of the reference transistor, and thus it is possible to improve the measurement accuracy.

In the twenty third and twenty fourth aspects of the invention, when the gate voltage of the charge detection transistor and that of the reference transistor decrease toward a level that causes the charge detection transistor and the reference transistor to turn off, the startup circuit controls the transistor in the output circuit to be maintained in the operating state, and thus it is possible to prevent a reduction in the output impedance. It is also possible to increase the rising speed of the transistor in a next measurement operation.

In the twenty fifth aspect of the invention, the bias voltages of the transistors in the respective cells are controlled by the reference current to the same value, and thus it is possible to reduce the cell-to-cell variation of the measurement accuracy. Thus, the measurement accuracy is improved.

In the twenty sixth aspect of the invention, a large drain current is supplied to a cell being in the measurement operation (being scanned) so as to achieve high measurement accuracy, while a small drain current is supplied to a cell in non-operation state (being not scanned). This makes it possible to reduce the consumption power while achieving high measurement accuracy.

According to the twenty seventh aspect of the invention, the substance detection apparatus can be used as a biosensor capable of detection various kinds of substance having a charge such as a bio substance.

REFERENCE NUMERALS

Figure 1:
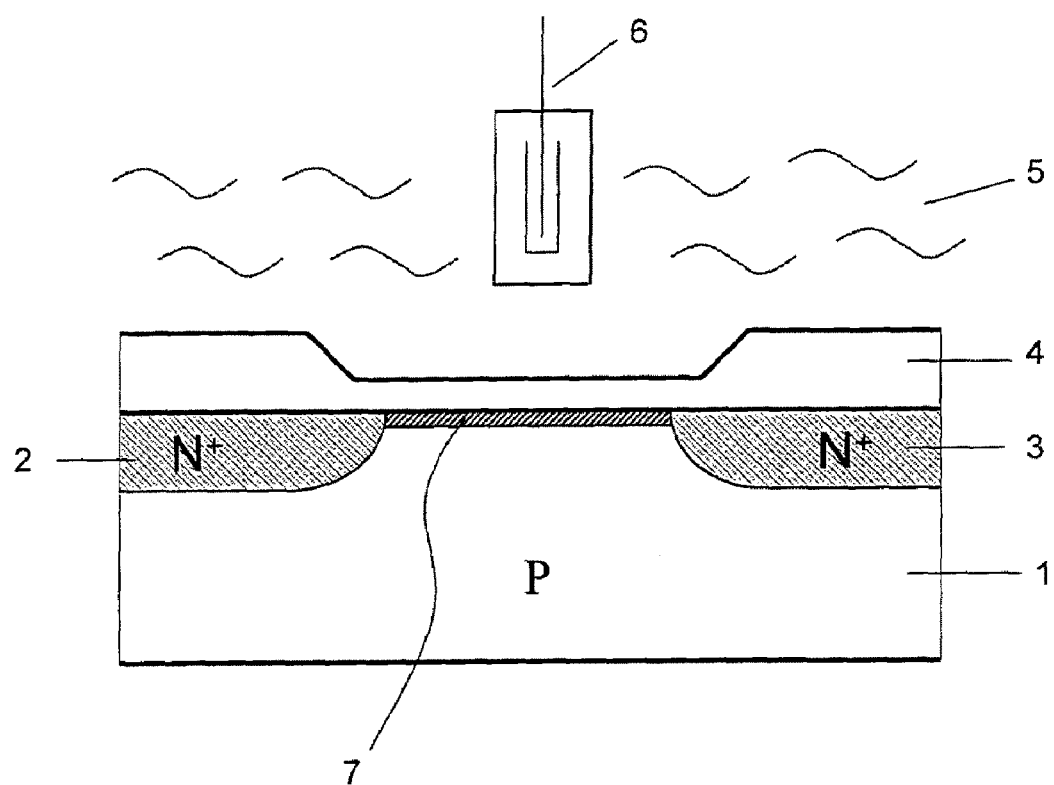
FIG. 1 is a cross-sectional view of a conventional charge detection transistor ISFET.

1: P substrate
2: source
3: drain
4: gate insulating film
5: solution
6: reference electrode
7: inversion layer
8: gate electrode
9: probe DNA
10: target DNA
R01, R02, R03, R1, R2, R3, R4, R5, R6, RL1, RL2, RLn: resistor
D1, D2: diode
MN1, MN2, MN3, MN4, MN7, MN8, MN10, MN11, MN20, MN21, MN22, MN23, MN24, MN25, MN26, MN27, MN28, MN30, MN31, MN32, MN33, MN40, MN41, MN42, MN43, MN50, MN51, MN52, MN53, MN54, MN55, MN101, MN102, MN103, MN104, MM110, MN111, MN112: N-type MOSFET
MP1, MP2, MP3, MP4, MP50, MP51, MP101, MP102, MP103, MP104, MP110, MP111: P-type MOSFET
DA1, DA2, DAn, Damp, D1, D2, D11, D12, D1n, D21, D22, D2n: differential amplifier
SW, SW1, SW2, SWn: switch
W1, W2, Wm: word line
B1, B2, Bn: signal bit line
G1, G2, Gn: grand bit line
R1, R2, Rn: reference line
C1, C2, Cn: calibration line

BEST MODES FOR CARRYING OUT THE INVENTION

The present invention is described in further below with reference to preferred embodiments of the present invention. Note that the present invention is not limited to the specific embodiments described below.

Embodiment 1

Figure 3:
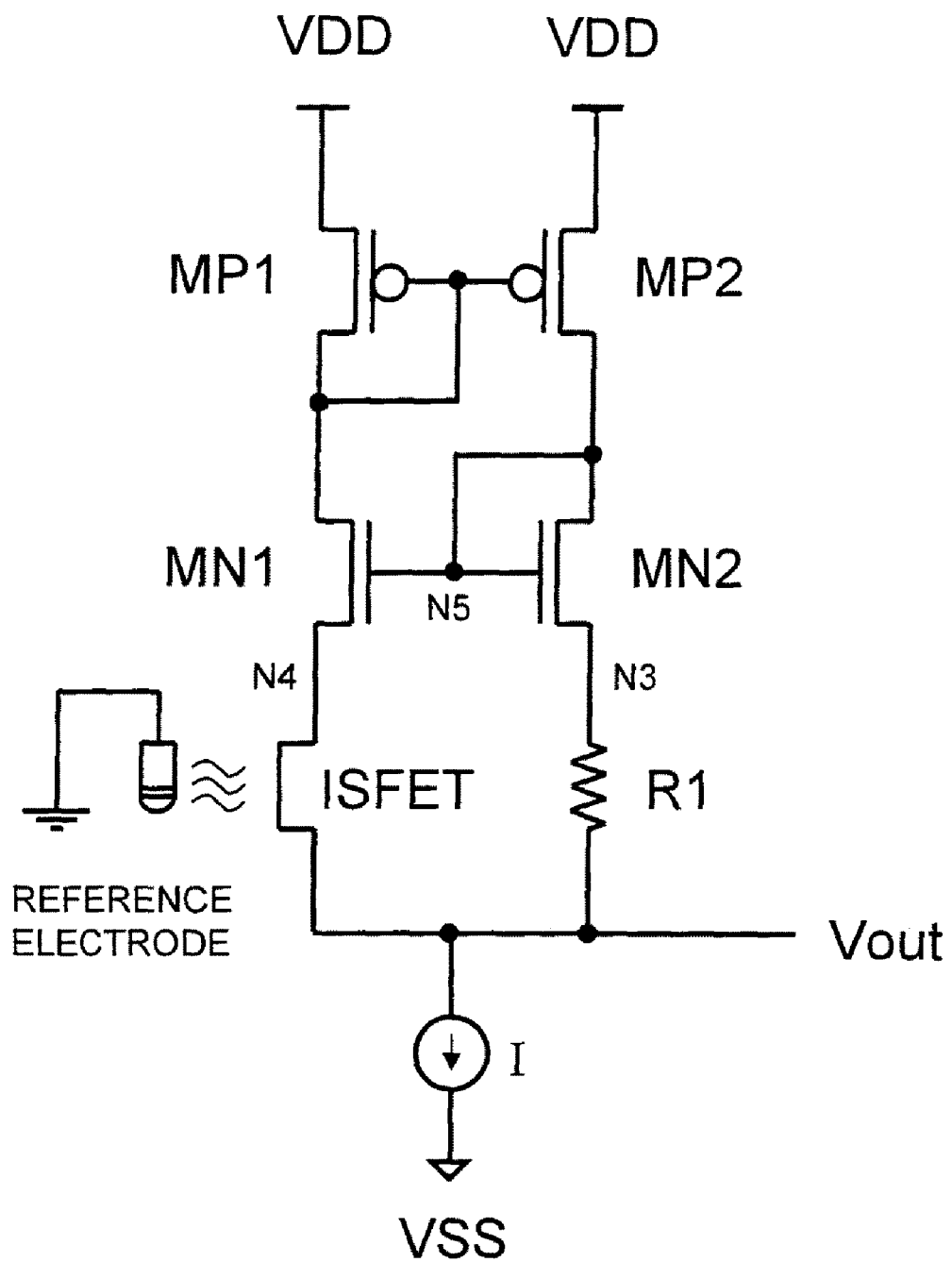
FIG. 3 is a diagram illustrating a basic circuit of a detection apparatus according to a first embodiment of the present invention.

FIG. 3 illustrates a basic circuit according to the present invention. Setting of bias for PMOSFETs MP1 and MP2 and NMOSFETs MN1 and MN2 is performed so that they always operate in saturation regions. MP1 and MP2 are formed at locations close to each other using transistors with the same size so that they have high similarity in characteristics. MN1 and MN2 are also formed at locations close to each other using transistors with the same size so that they have high similarity in characteristics. MP1 and MP2 form a first current mirror circuit, and MN1 and MN2 form a second current mirror circuit. By these current mirror circuit, currents are controlled such that a current flowing through MP1, MN1, and ISFET and a current flowing through MP2, MN2, and a first resistor R1 are equally set to I/2. Note that ISFET serves as a detection field effect transistor. In the present description, hereinafter, PMOSFETs are each simply denoted by a symbol MP suffixed with a number, and NMOSFETs are simply denoted by a symbol MN suffixed with a number.

Figure 2:
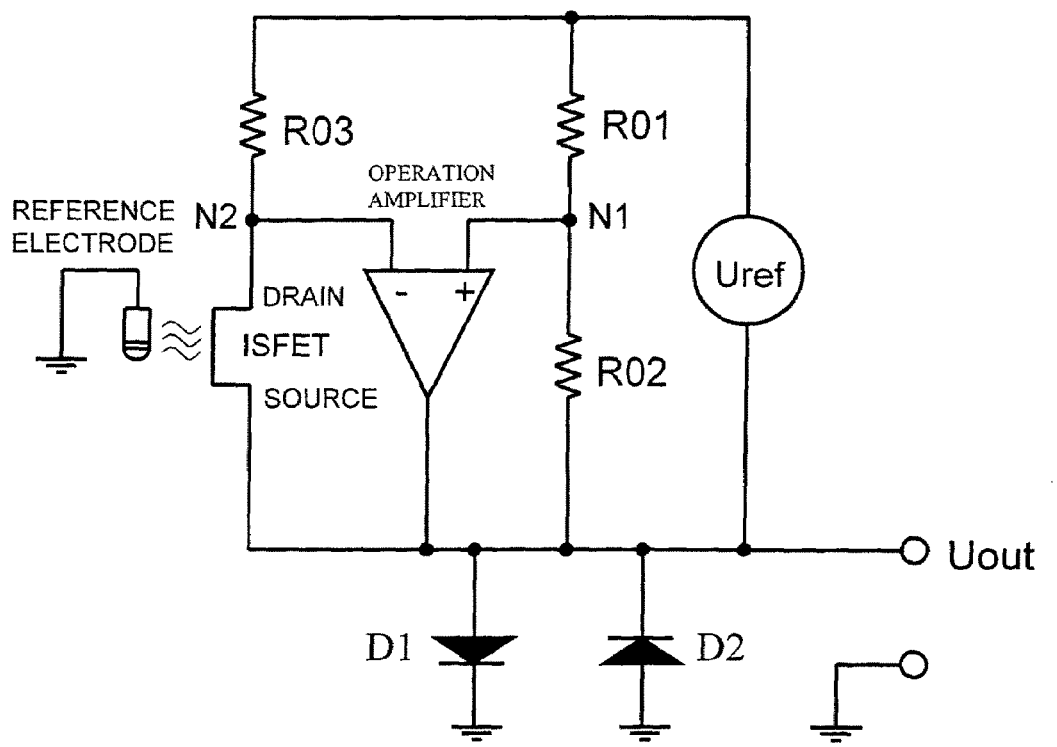
FIG. 2 is a diagram illustrating a conventional circuit adapted to control a charge detection transistor.

In the case where the current flowing through MN1 is equal in magnitude to the current flowing through MN2, the voltage at a node N3 and the voltage at a node N4 are respectively equal to the value given by subtracting a threshold value of MN1 or MN2 and an overdrive voltage from the voltage at a node N5. Therefore, when MN1 and MN2 are equal in characteristics, N3 and N4 are at an equal voltage. Thus, a constant current equal to I/2 flows through the ISFET and a constant voltage equal to R1·I/2 is applied between the drain and the source of the ISFET. The reference electrode is maintained at a fixed ground level and an output voltage Vout is determined depending on the operating point of the ISFET. By setting voltages such that VDD=3V and VSS=−1.3V, the source voltage of the ISFET is limited to a range from −1.3 to 3 V. As can be seen from the above description, the same functions as those of FIG. 2 can be achieved by the circuit shown in FIG. 3. The circuit shown in FIG. 3 can be realized in a small area using a CMOS integrated circuit, and has an advantage, over a circuit using an operational amplifier, that there is no factor that can cause an instable operation such as oscillation. Note that the resistor R1 may be replaced with a transistor or a diode. Use of a transistor or a diode makes it possible to reduce the element size and increase the cell integration density.

(Circuit with Improved Channel Length Modulation Effects)

Figure 4A:
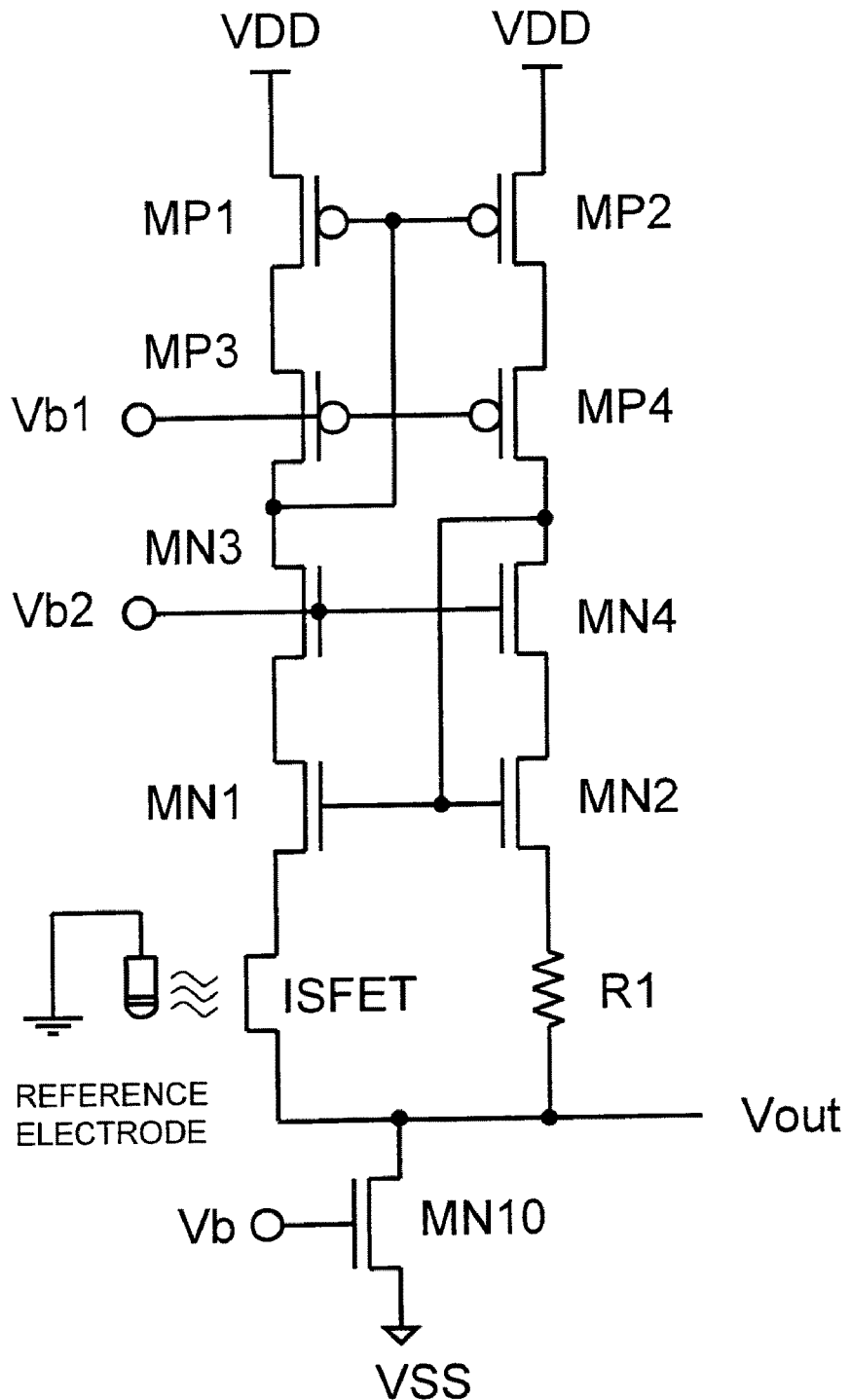
FIG. 4A is a diagram illustrating another example of a detection apparatus according to the first embodiment of the present invention.

In the circuit shown in FIG. 3, the channel length modulation effect of MOSFETs MP1, MP2, MN1, and MN2 can lead to a difference in current between the two paths and a difference in potential between the nodes N3 and N4, which makes it difficult to achieve a desired characteristic. FIG. 4A illustrates a circuit configured to reduce the above disadvantage. This circuit includes additional PMOSFETs MP3 and MP4 and additional NMOSFETs MN3 and MN4. These additional transistors MP3, MP4, MN3, and MN4 are connected in a cascode fashion to MP1, MP2, MN1, and MN2. MP1, MP2, MP3, and MP4 form a first current mirror circuit, and MN1, MN2, MN3, and MN4 form a second current mirror circuit. The cascode connection employed allows the channel length modulation effect to be reduced to 1/(gm·ro), where gm and ro are the transconductance and the output resistance of MN3, MN4, MP3, and MP4. The product gm·ro has a value of about 30. MN10 serves as a current source that generates a current I. The operating regions of MP1, MP2, MP3, MP4, MN1, MN2, MN3, MN4, and MN10 are always within saturation regions.

Figure 5A:
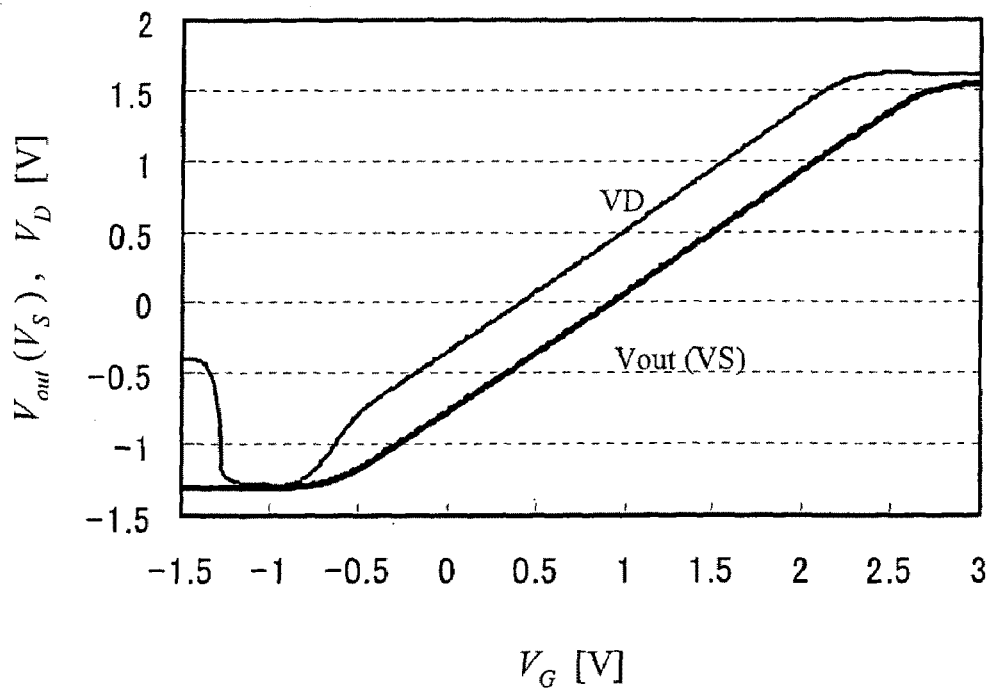
FIG. 5 is a characteristic diagram illustrating operating waveforms of the circuit shown in FIG. 4A.
Figure 5B:
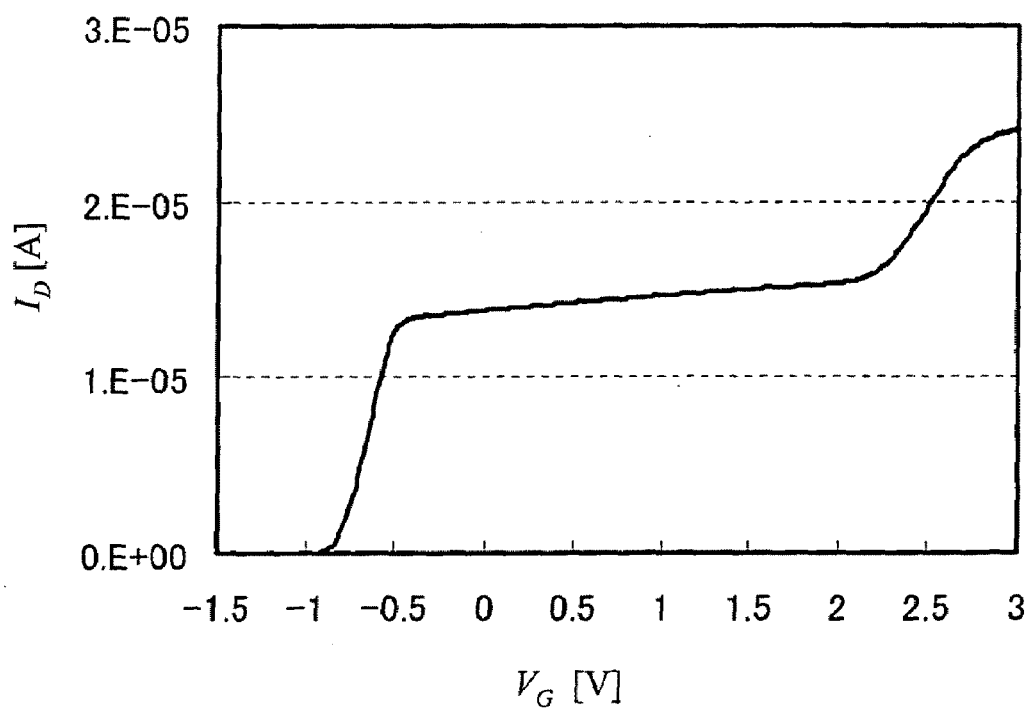

A circuit was actually produced using a standard 0.35 μm CMOS process. Design parameters and results of the production are described below. The design power supply voltages were determined such that VDD=3V and VSS=−1.3V, the design drain-source voltage of the ISFET was set to 0.45 V, and the design drain current was set to 15 μA. According to these design values, the resistance of R1 was determined to be 30 KΩ. The gate width of each transistor was determined so that the drain saturation voltage was less than 0.2 V, and the channel length was set to 1 μm so that the channel length modulation effect was reduced. That is, MP1, MP2, MP3, and MP4 were each formed by a PMOSFET having a channel length of 1 μm and a gate width of 10 μm, MN1, MN2, MN3, and MN4 were each formed by a NMOSFET having a channel length of 1 μm and a gate width of 4 μm, and an NMOSFET with a channel length of 1 μm and a gate width of 10 μm was employed as MN10. Vb was adjusted so that the current flowing through MN10 was equal to 30 μA, and more particularly, Vb was set to −0.63V. To achieve the operation in the saturation region, Vb1 and Vb2 were set such that Vb1=1.8V and Vb2=3V. FIG. 5 illustrates operating waveforms. VG denotes the potential at a point on the gate insulating film of the ISFET. The source voltage VS of the ISFET was proportional to VG in the range of VG from −0.5 V to 2.2 V, and the difference between the drain voltage VD and VS was substantially maintained to the design value 0.45 V.

In this region, the drain current ID of the ISFET was kept at about 15 μA. Due to a substrate bias effect, the gradient of VS with respect to VG was smaller than 1 (was equal to about 0.85). An effective method to delete this dependence on the substrate voltage is to use an N-type substrate or use a triple-well structure and each P-well layer is connected to the source of an ISFET.

Also in the circuit shown in FIG. 4A, the resistor R1 may be replaced with a transistor or a diode.

Table 1 shows parameters of the circuit shown in FIG. 4A.

TABLE 1

| Design parameter | | Design value | |
| --- | --- | --- | --- |
| Power source | VDD | 3 | V |
|  | VSS | −1.3 | V |
|  | Vb | −0.63 | V |
|  | Vb1 | 1.8 | V |
|  | Vb2 | 3 | V |
| ISFET | ID | 15 | μA |
|  | VDS | 0.45 | V |
| Resistor | R1 | 30 | kΩ |
| PMOSFET | MP1, MP2, | L = 1 | μm |
|  | MP3, MP4 | W = 10 | μm |
| NMOSFET | MN1, MN2, | L = 1 | μm |
|  | MN3, MN4 | W = 4 | μm |
|  | MN10 | L = 1 | μm |
|  |  | W = 10 | μm |

Figure 4B:
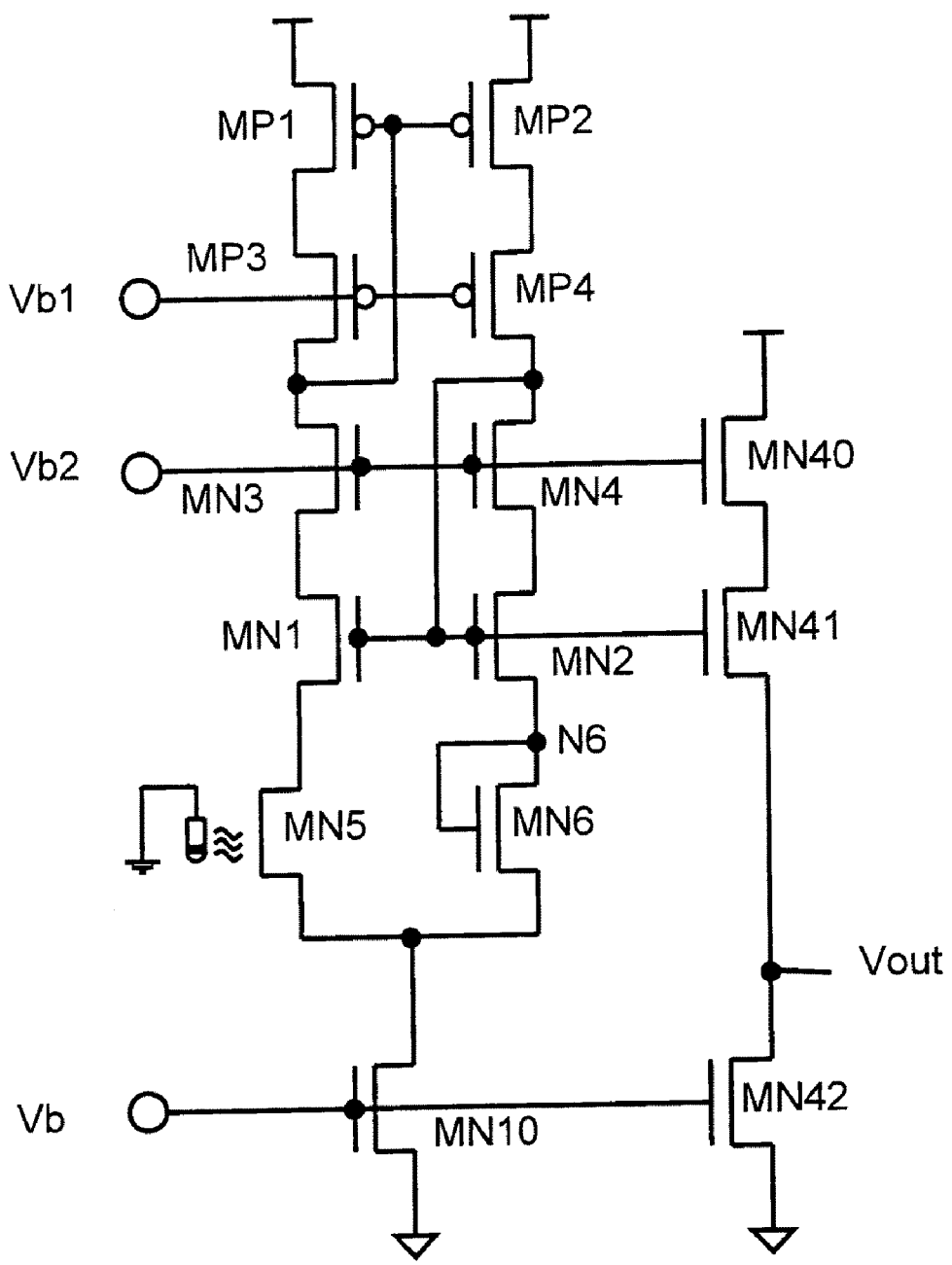
FIG. 4B is a diagram illustrating another example of a detection apparatus according to the first embodiment of the present invention.

FIG. 4B illustrates an example of a circuit obtained by replacing the resistor R1 in the circuit shown in FIG. 4A with a first transistor. In FIG. 4B, the gate voltage of MN1 and MN2 is given as an input, and an output voltage Vout is provided via a source follower of a cascode connection of MN40, MN41, and MN42. This circuit formed by MN40, MN41, and MN42 serves as a second output circuit. As will be described later, when a reference circuit is used, a circuit identical in configuration thereto for a reference field effect transistor serves as a first output circuit. When MN5 and MN6 have the same characteristics, the gate voltage of MN5 is equal to the voltage of a node N6. When MN1, MN2, and MN41 have the same characteristics, Vout is equal to the voltage of a node N6. Thus, Vout is nearly equal to the gate voltage of the ISFET. MN5 and MN6, and also MN1, MN2, and MN41, are formed at close locations in a cell so that similar characteristics are achieved, and thus it is possible to suppress the influence of the variation in threshold value and the substrate bias effect on the output.

(Bias of Cascode-Connected Transistors)

Figure 6:
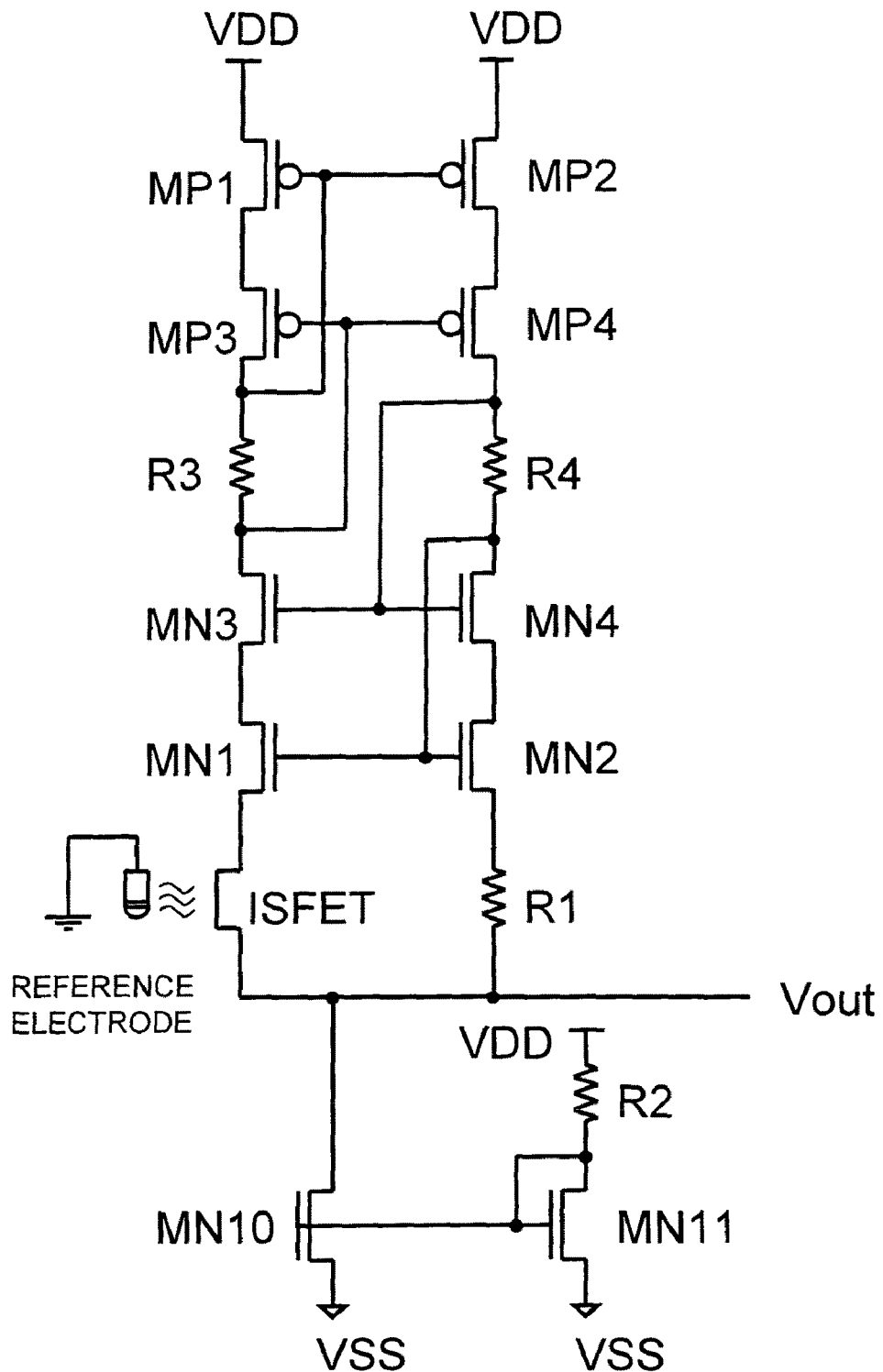
FIG. 6 is a diagram illustrating another example of a detection apparatus according to the first embodiment of the present invention.

The circuit shown in FIG. 4A needs voltage source voltages VDD and VSS and further three bias voltages Vb, Vb1, and Vb2. FIG. 6 illustrates a circuit in which these voltages are generated automatically. A current source is formed by a resistor R2 serving as a fourth resistor and a current mirror configured by MN11 and MN10. A current flowing through MN10 is controlled by the current mirror such that it becomes equal to a current flowing through NMOSFET MN11. The current flowing through MN11 is determined by the resistor R2 and the transistor MN11 diode-connected to the resistor R2. If the diode voltage of MN11 is neglected, then the current is given by I=(VDD−VSS)/R2. A second resistor R3 is set such that a voltage appearing across the resistor R3 is greater than a saturation drain voltage D of MP1, that is, R3 is set such that R3>2D/I. Similarly, a third resistor R4 is set such that a voltage appearing across the resistor R4 is greater than a saturation drain voltage D of MN2, that is, R4 is set such that R4>2D/I.

The voltage drop across R3 is applied between the source and the drain of MP1 and MP2, and the voltage drop across R4 is applied between the source and the drain of MN1 and MN2. This causes the transistors of the current mirror to be biased such that the transistors operate in the saturation region. Thus, a constant drain current I/2 flows through the ISFET, and a constant drain-source voltage VDS=IR1/2 is applied to the ISFET. The voltages generated across the resistors R3 and R4 and the drain-source voltage of the ISFET are determined approximately by the resistance ratios R3/R2, R4/R2, and R1/R2. By forming these resistors using the same material, it is possible to reduce the influence of temperature-dependent variations of resistors and MOSFET characteristics.

Figure 7A:
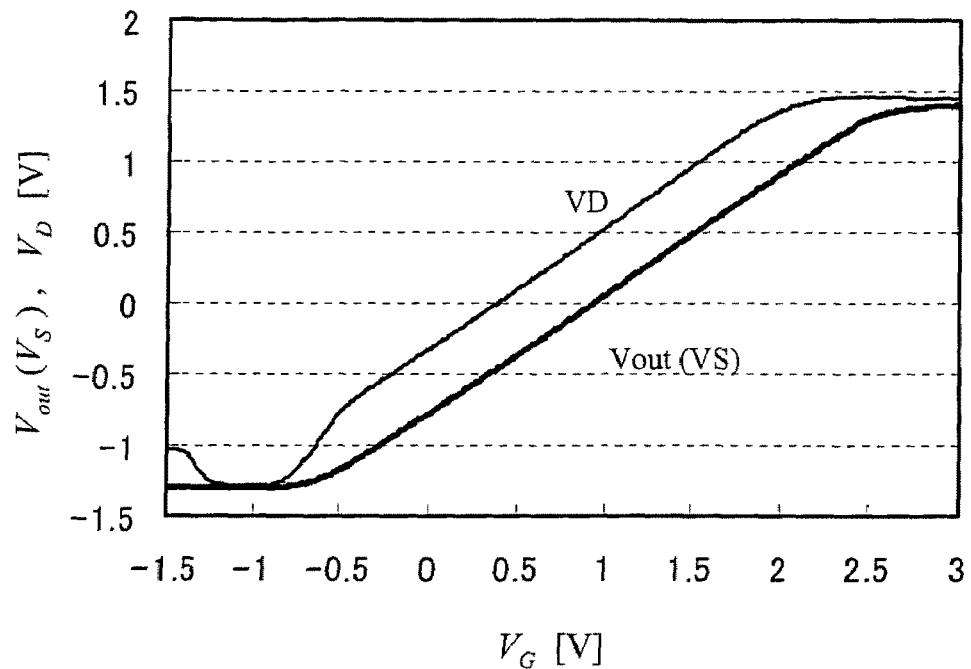
FIG. 7 is a characteristic diagram illustrating operating waveforms of the circuit shown in FIG. 6.
Figure 7B:
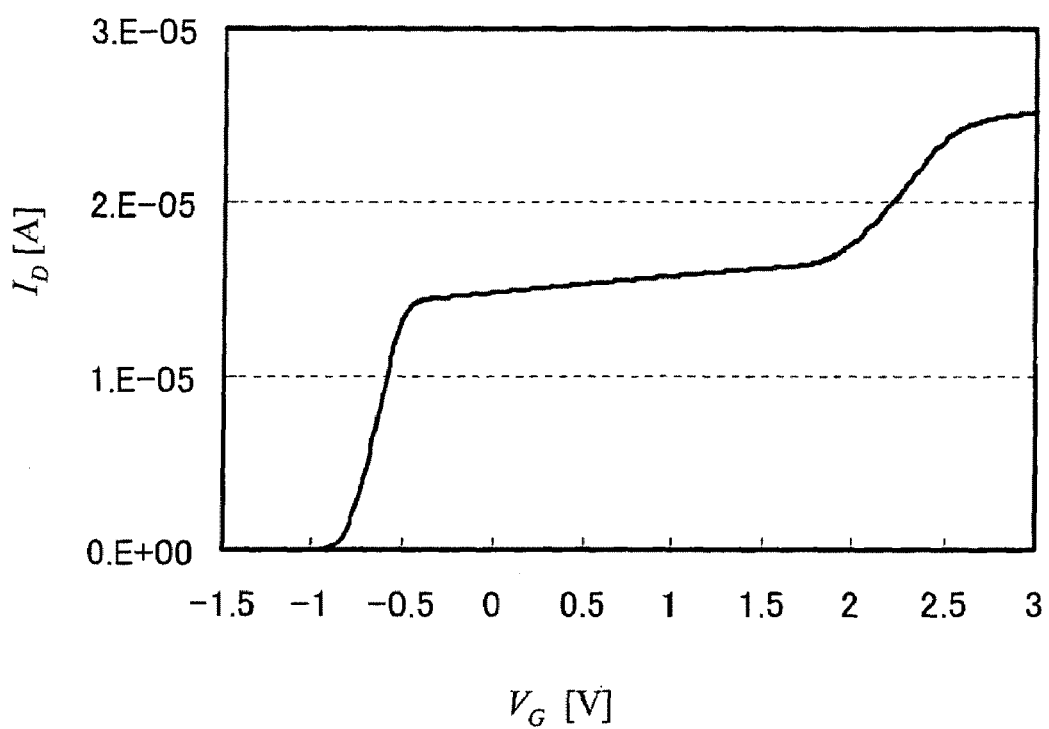

However, the current flowing through the ISFET is influenced by a temperature-dependent change in resistance R2. In design, parameters of elements similar to those shown in FIG. 4A were set to values similar to those employed in the circuit shown in FIG. 4A, while R2 was set to 120 kΩ, and R3 and R4 were set to 15 kΩ. A resistor with a resistance of 30 kΩ was employed as a basic resistor element, and resistors were formed using basic resistor elements. That is, R1 with a resistance of 30 kΩ was formed using one basic resistor element. R2 was formed by a series connection of four basic resistor elements, and R3 and R4 were each formed by a parallel connection of two basic resistor elements. This allowed R1, R2, R3, and R4 to be maintained constant in ratio, for total resistance including all resistance components such as sheet resistance and contact resistance. For MN11, as with MN10, an NMOSFET having a channel length of 1 μm and a gate width of 10 μm was used. Because the currents flowing through MN10 and MN11 were set to 30 μA, when the power source voltages were set such that VDD=3V and VSS=−1.3V, the total power consumption for the 16×16 matrix array was given by 16×16×2×30 μA×4.3 V=66 mW. FIG. 7 illustrates operating waveforms of the circuit. The addition of resistors R3 and R4 causes the upper limit of the operation range to decrease to 1.8 V from that of 2.2 shown in FIG. 5. However, it is possible to reduce noise applied to the circuit compared with the case in which the bias is supplied externally.

Table 2 shows circuit parameters of the circuit shown in FIG. 6.

TABLE 2

| Design parameter | | Design value | |
| --- | --- | --- | --- |
| Power source | VDD | 3 | V |
|  | VSS | −1.3 | V |
| ISFET | ID | 15 | μA |
|  | VDS | 0.45 | V |
| Resistor | R1 | 30 | kΩ |
|  | R2 | 120 | kΩ |
|  | R3, R4 | 15 | kΩ |

TABLE 2-continued

| Design parameter | | Design value |
|---|---|---|
| PMOSFET | MP1, MP2, MP3, MP4 | L = 1 μm<br>W = 10 μm |
| NMOSFET | MN1, MN2, MN3, MN4 | L = 1 μm<br>W = 4 μm |
| | MN10, MN11 | L = 1 μm<br>W = 10 μm |

In the circuit shown in FIG. 6, resistors R3 and R4 may be replaced with a transistor or a diode. Also in this case, use of a transistor or a diode makes it possible to reduce the element size and increase the cell integration density per area.

Figure 8:
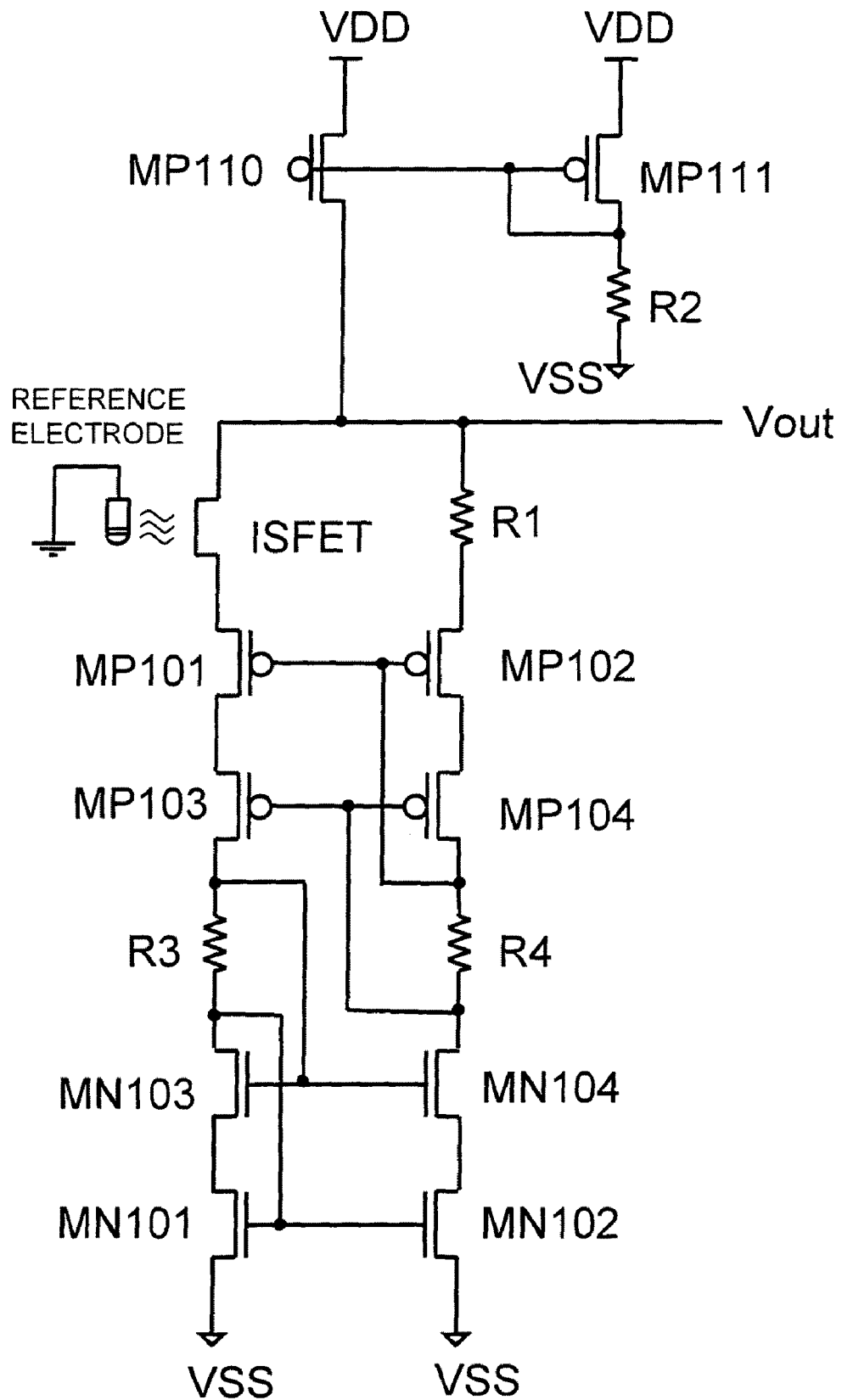
FIG. 8 is a diagram illustrating another example of a detection apparatus according to the first embodiment of the present invention.

In the circuit shown in FIG. 6, the linear output voltage range is from 1.2 V (VDD−VT−4D−VDS) to −1.1 V (VSS+D), and there is a significant limitation on the operation in a high-voltage region. To expand the high-voltage detection region, PMOSFETs and NMOSFETs may be exchanged as in a circuit shown in FIG. 8. In the circuit shown in FIG. 8, the linear output voltage range is from 2.8 V (VDD−D) to 0.5 V (VSS+VT+4D+VDS). Also in the circuit shown in FIG. 8, resistors R3 and R4 may be replaced with a transistor or a diode.

(Overall Circuit Configuration of Detection Apparatus)

Figure 9:
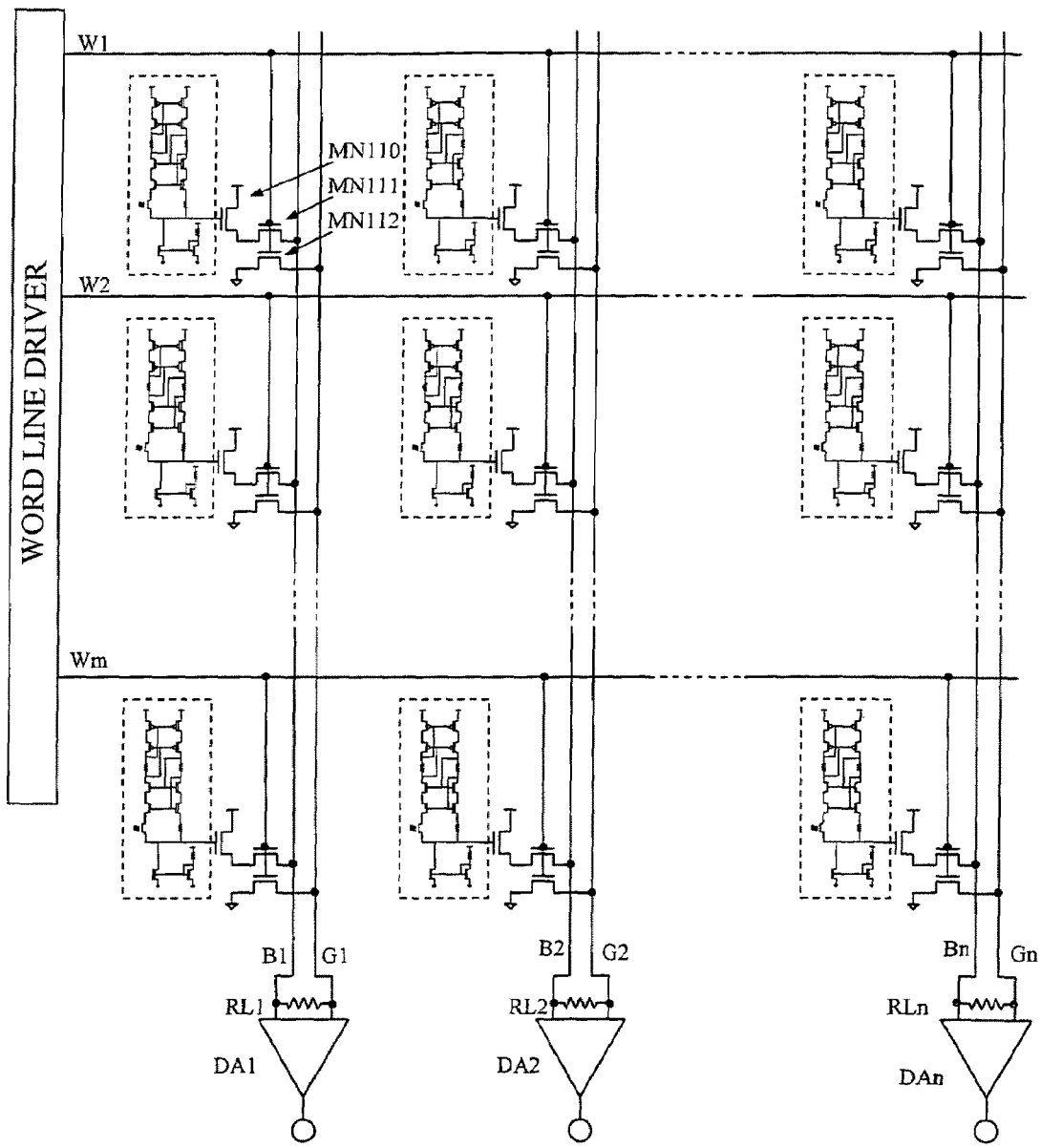
FIG. 9 is a circuit diagram illustrating an embodiment of a detection apparatus configured by disposing circuits, each similar to the circuit shown in FIG. 6, in the form of a matrix array.

FIG. 9 illustrates a circuit including a matrix array of cells each of which is similar to the circuit shown in FIG. 6. Voltages of word lines W1, W2, . . . , Wm are generally set to the OFF gate voltage (for example, VSS) of the transistors MN111 and MN112. When a particular row is selected, a corresponding one of the word lines is set to the ON gate voltage (for example, VDD). In the following discussion, by way of example, it is assumed that the first row is selected, and the word line W1 is applied with VDD, and word lines W2, . . . , Wm are applied with VSS. In this state, pass gate transistors MN111 and MN112 are in ON states and cell signals of this row are output over bit line pairs (B1, G1), (B2, G2), . . . , (Bn, Gn). The output voltage of each ISFET is received by a source follower MN110 that serves as an output transistor, and the signal is transferred in a current mode to differential amplifiers DA1 to DAn whereby the current is returned to the cell and to the ground. MN112 functions as a feedback transistor. Bit lines B1 to Bn are signal lines, and bit lines G1 to Gn are feedback lines. This configuration reduces effects of common node noise. Resistors RL1, RL2, . . . , RLn are inserted between bit line pairs of the current paths, and the voltage differences across the respective resistors are amplified by the differential amplifiers DA1, DA2, . . . , DAn. These differential amplifiers function as the third differential amplifier.

Figure 10:
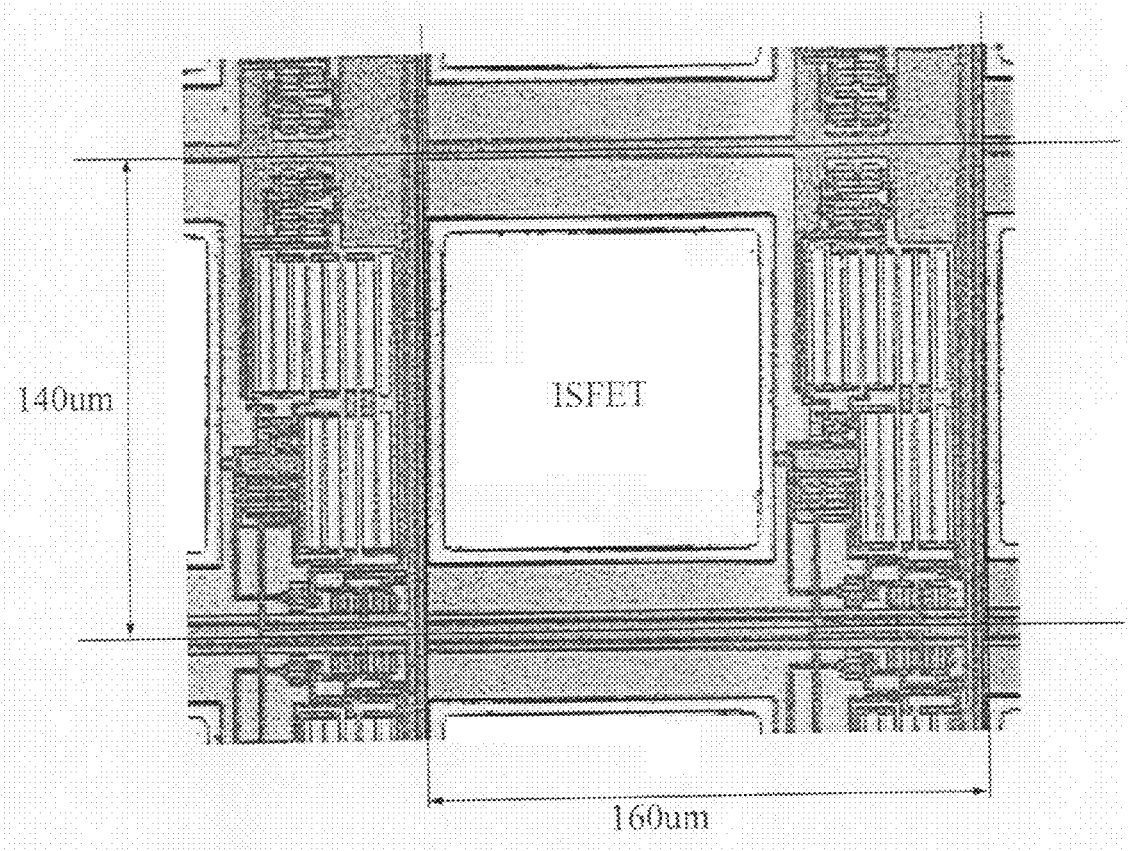
FIG. 10 is a layout diagram illustrating one of cells shown in FIG. 9.

FIG. 10 illustrates a layout of one cell in the circuit shown in FIG. 9. The ISFET has a size of 100 μm×100 μm, and the size of the cell including the control circuit is 160 μm×140 μm. To reduce the temperature-dependent change in characteristic, the resistor R2 is formed by a series connection of four resistors R1, and the resistors R3 and R4 are each formed by a parallel connection of two resistors R1. To reduce the variation in size of produced resistors, dummy resistors are provided at both ends of each resistor.

Embodiment 2

Figure 11:
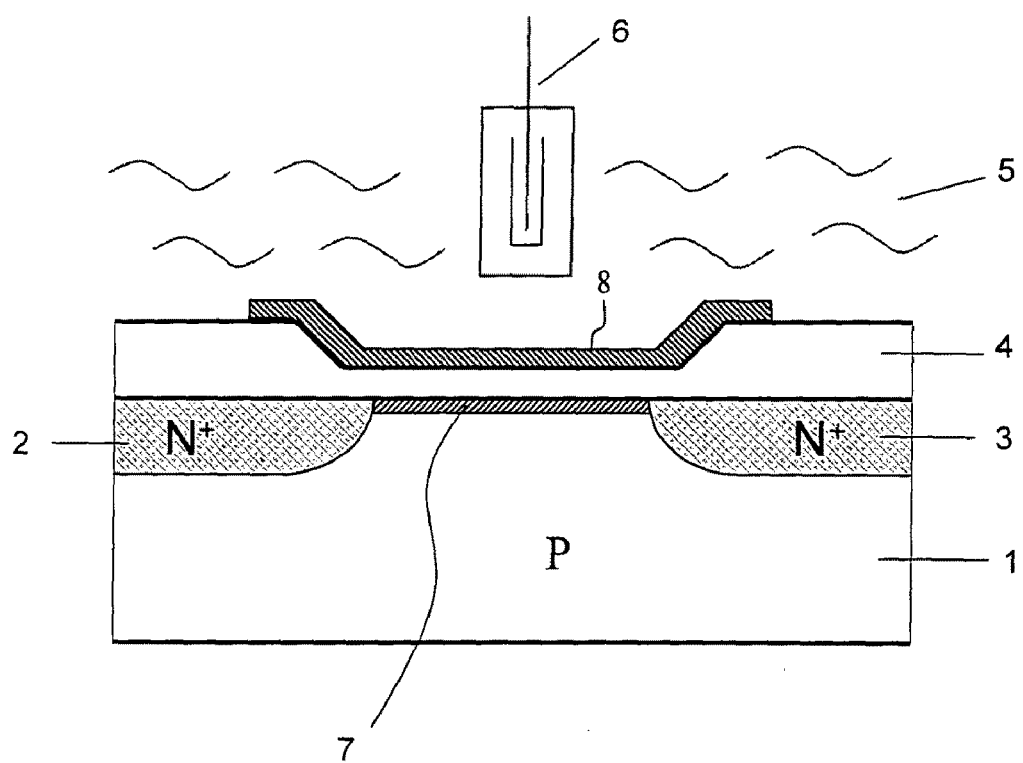
FIG. 11 is a cross-sectional view of a conventional charge detection transistor ISFET with a gate electrode.

The charge detection transistor shown in FIG. 1 has the configuration in which a solution 5 is in direct contact with the gate insulating film 4. Alternatively, the charge detection transistor may include a gate electrode 8 formed on the gate insulating film 4 as shown in FIG. 11. A technique of DNA detection using a charge detection transistor having a gate electrode is disclosed, for example, in "Electrical detection of biomolecular interactions with metal-insulator-semiconductor diodes" (P. Estrtela, P. Migliorato, H. Takiguchi, H. Fukushima, and S. Nebashi, Biosensors and Bioelectronics 20 (2005) pp. 1580-1586).

In this configuration, the gate electrode 8 is used in a floating state. By applying a charge in an initial state, it is possible to compensate for a variation in threshold value or in an initial charge, and it is also possible to adjust the operating point of the transistor at an optimum point.

Figure 12:
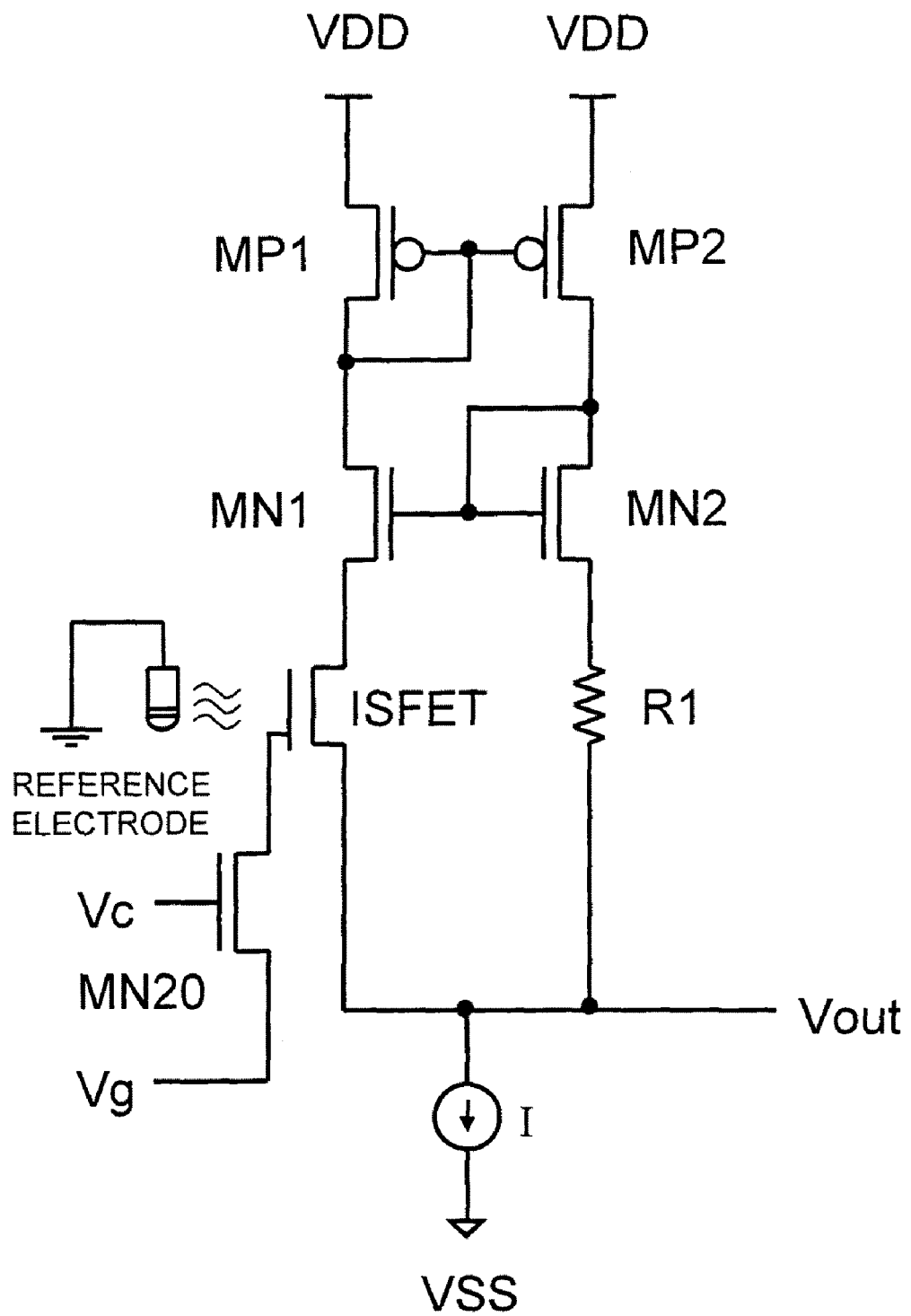
FIG. 12 is a diagram illustrating a basic circuit of a detection apparatus according to a second embodiment of the present invention.

FIG. 12 illustrates a basic circuit using an ISFET with a gate electrode according to the present invention. This ISFET functions as the charge detection field effect transistor having the gate electrode. The gate electrode is connected to a bias voltage Vg via a MOSFET MN20. MN20 functions as the charging transistor or the second charging transistor. An ON gate voltage (for example, VDD) is first applied to Vc whereby the transistor MN20 is turned on and thus the voltage of the gate electrode is set to Vg. Thereafter, an OFF gate voltage (for example VSS) is applied to Vc thereby to turn off the transistor MN20. By setting the OFF drain current of the transistor MN20 to a small value, it is possible to maintain the charge on the gate electrode of the ISFET for a predetermined period. For example, when the gate electrode of the ISFET has a size of 100 μm×100 μm, capacitance due to a solution is about 1 nF. For well designed transistors, it is possible to achieve as small an OFF current as 10 fA or smaller including a variation. Such a small OFF current makes it possible to maintain the charge on the gate electrode of the ISFET for one whole day or longer. To maintain the charge for a longer period, it is effective to set Vg to a voltage close to the voltage of the gate electrode of the ISFET when the transistor MN20 is in an OFF state.

(Example of Circuit Including Reference Field Effect Transistor)

Figure 13:
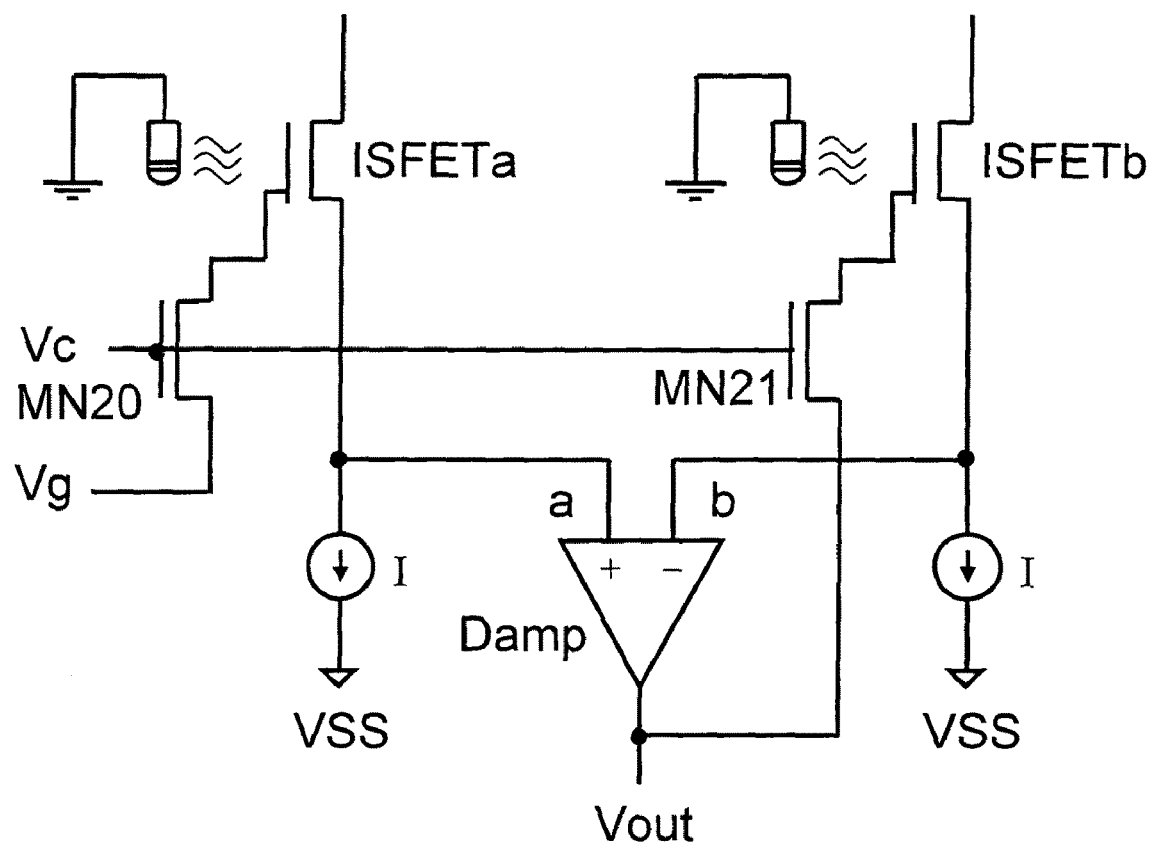
FIG. 13 is a diagram illustrating another example of a basic circuit of a detection apparatus according to the second embodiment of the present invention.

FIG. 13 illustrates a circuit configuration in which two ISFETs each having a gate electrode are used. ISFETa is a reference field effect transistor with a gate electrode, and ISFETb is a charge detection field effect transistor with a gate electrode. Initially, an ON gate voltage is applied to Vc thereby to turn on transistors MN20 and MN21. MN20 is a first charging transistor, and MN21 is a second charging transistor. Outputs a and b from the two circuits are input to a differential amplifier Damp, and an output of the differential amplifier Damp is fed back to the gate electrode of ISFETb via MN21. In this manner, the difference in threshold value between ISFETa and ISFETb is automatically compensated for so that voltages a and b become equal. Thereafter, an OFF gate voltage is applied to Vc thereby to turn off MN20 and MN21. ISFETa is used to provide a reference, and ISFETbs used to detect a change in charge. The difference between the output voltages of ISFETa and ISFETb is amplified by the differential amplifier Damp, and the resultant amplified signal is output. The differential amplifier Damp functions as the fourth differential amplifier or the first differential amplifier. This configuration allows a charge to be detected with high accuracy. In the present example, the compensation and the outputting are performed by the same single differential amplifier Damp. Alternatively, to separately optimize the compensation accuracy and the detection input voltage range, two differential amplifiers having different gains may be used or an amplifier may be inserted between the output of the differential amplifier Damp and the transistor MN21. Furthermore, although the output signals are given by the voltage at the source terminal of ISFETa and the voltage of the source terminal of ISFETb, the output signals may be given by other voltages that change according to the gate voltage of these transistors ISFETa and ISFETb.

(Example of DNA Detection Apparatus)

Figure 14:
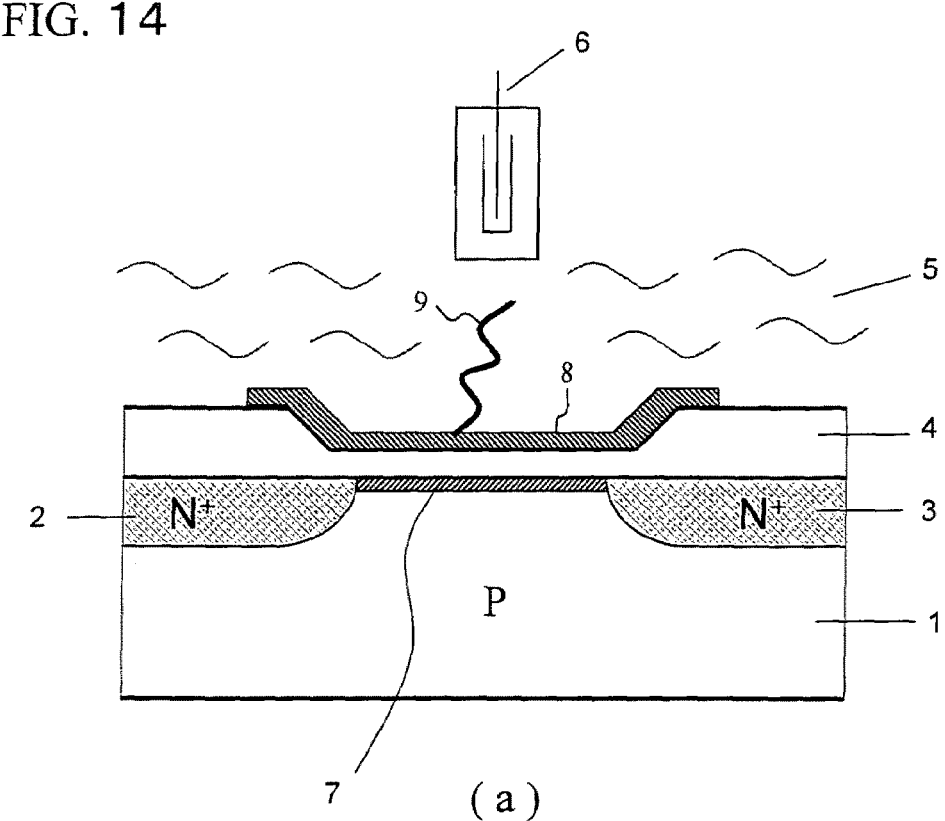
FIG. 14 is a diagram illustrating a principle of DNA detection using the circuit shown in FIG. 13, wherein (a) illustrates a state in which a probe single strand DNA 9 is in contact with the circuit, and (b) illustrates a state in which the DNA 9 has been hybridized with a target DNA 10.
Figure 14:
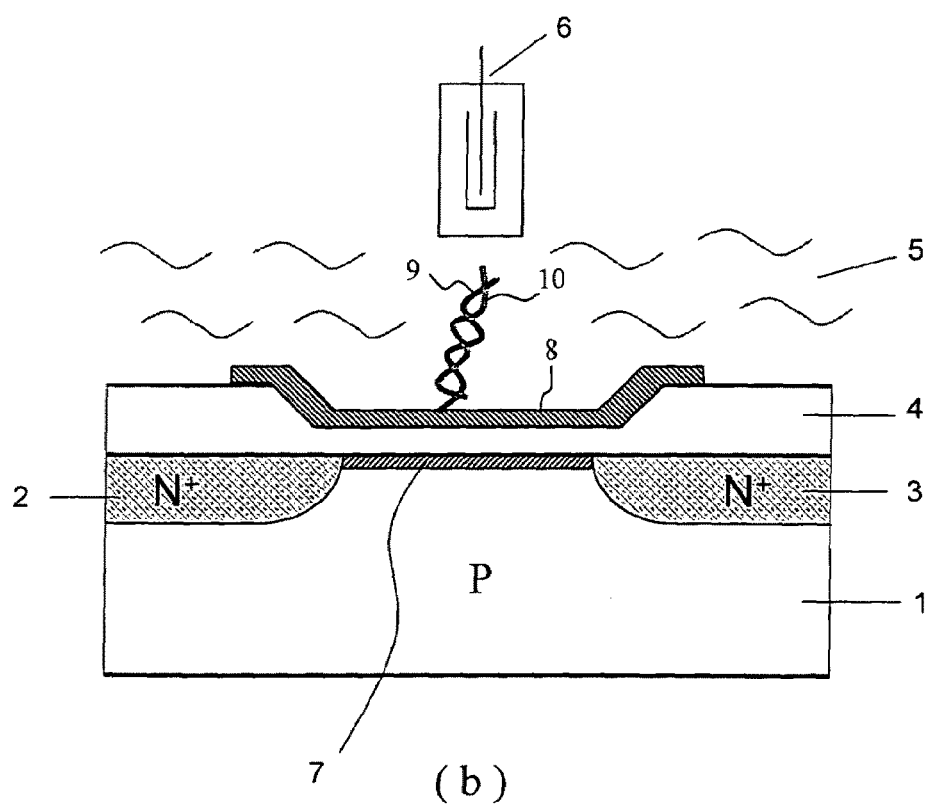

With reference to FIG. 14, a method of detecting DNA is described in further detail below. DNA is normally in the form of a double helix. However, at a temperature higher than a melting temperature (20° C. to 90° C. (depending on the base sequence)), DNA is separated into two strands. At temperatures lower than the melting temperature, when two strands have complementary base sequences, a double helix is formed. Each single strand has a charge of −e (e denotes an amount of elementary electric charge) per length of 0.34 nm.

First, as shown in FIG. 14(a), a single strand 9 (probe DNA) having a known base sequence is firmly put on an electrode 8. For example, the surface of the electrode 8 is formed of gold, and an end part of DNA 9 is thiolated and bonded with gold via sulfur. Thereafter, the detection apparatus is soaked in a buffer solution, and an ON gate voltage is supplied to Vc shown in FIG. 13 so that the two ISFETs save equal output voltages a and b. This makes it possible to compensate not only for a variation in threshold value of ISFETs but also for a variation in charge caused by a difference in adhesion of DNA. Thereafter, an OFF gate voltage is applied to Vc whereby the gate electrode 8 is brought into a floating state. In this state, if no change occurs in states of ISFETa and ISFETb, the voltages a and b are maintained at the same value.

After that, a single strand of DNA 10 to be examined (target DNA) is added only to the solution in which the gate electrode of ISFETb is located. When the solution containing the added target DNA flows over the electrode of ISFETb, the temperature is maintained lower than the melting temperature to enhance the formation of a double helix. The addition of DNA is then stopped, and a further buffer solution is supplied such that the target DNA 10 remaining without being combined is carried away. If the target DNA 10 has a base sequence complementary with the base sequence of the probe DNA 9, a double helix is formed and the target DNA 10 is fixed.

The amount of charge of the DNA increases by a factor of about 2 in the state (b) of FIG. 14 in comparison with the state (a) of FIG. 14. Only a buffer solution including no target DNA is always supplied onto the gate electrode of ISFETa shown in FIG. 13. As a result, signals corresponding to the states of (a) and (b) in FIG. 14 appear as the signals a and b in FIG. 13, and the difference between these signals is amplified by the differential amplifier. Thus, it is possible to accurately detect whether there is a double helix of DNA.

This method using the differential amplifier has the advantage that even if a change occurs in threshold value of ISFETs due to a change in environment such as a change in temperature, the change in threshold value is equal for ISFETa and ISFETb and thus it is possible to obtain an output that does not depend on the change in environment. In applications in which the temperature changes from room temperature to 100° C. or in applications in which the chip is brought into contact with solutions having different components as with the case of the biochip, it is possible to detect only a change in charge in the solution, which allows high accuracy in detection.

Figure 15:
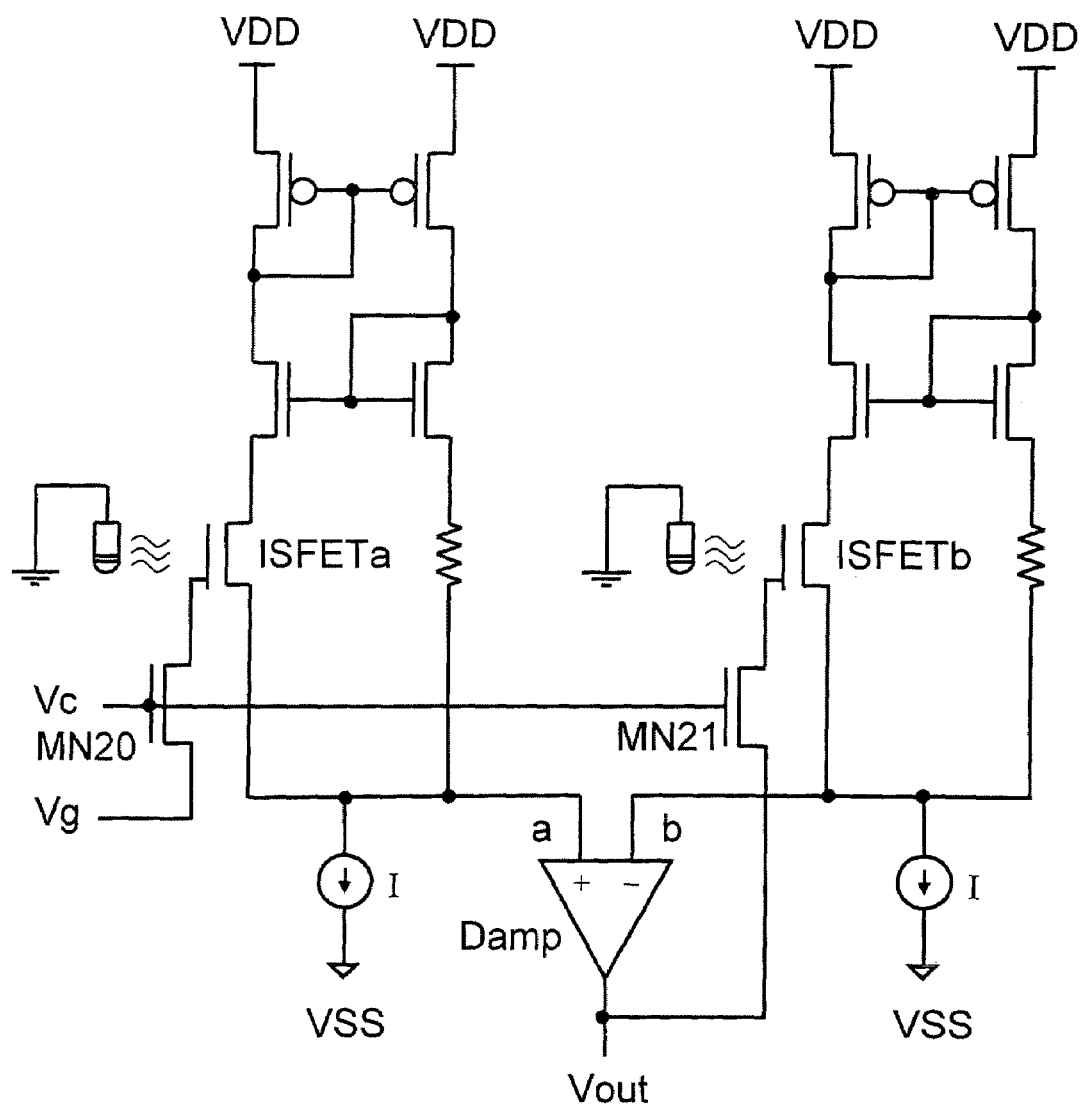
FIG. 15 is a diagram illustrating another example of a detection apparatus configured by combining the circuits shown in FIG. 12 and FIG. 13 according to the second embodiment of the present invention.

FIG. 15 illustrates a configuration obtained by combining the circuit shown in FIG. 12 and the circuit shown in FIG. 13. The source-drain voltages of ISFETs are maintained at a relatively low value (for example, 0.5 V) so that injection of carries into the gate insulation film or generation of surface states due to a high electric field does not occur, whereby a high-stability operation is achieved.

Figure 16:
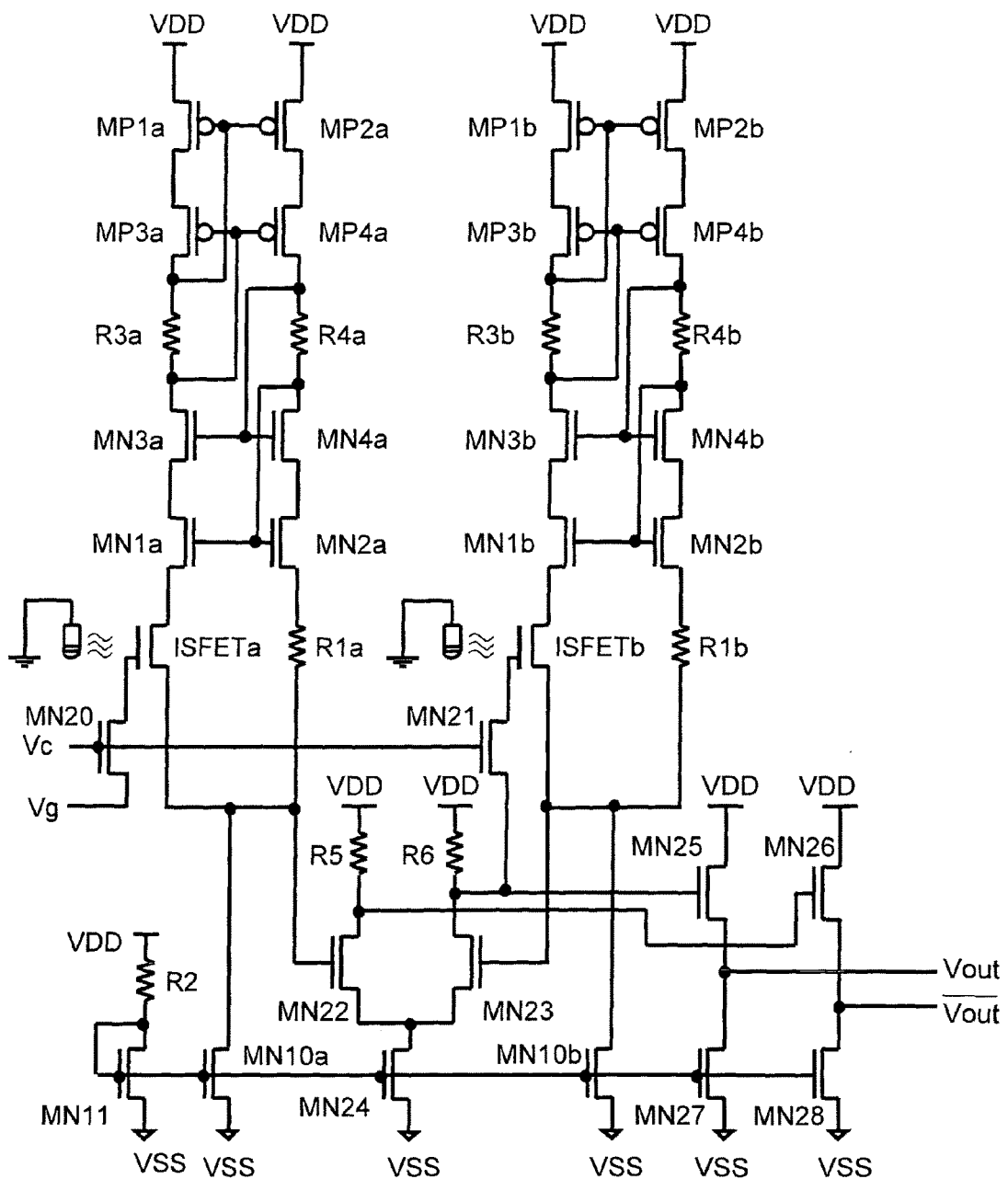
FIG. 16 is a diagram illustrating another example of a detection apparatus according to the second embodiment of the present invention.

FIG. 16 illustrates a specific example of a circuit. In FIG. 16, transistors and resistors similar to those shown in FIG. 6 have similar structures. As for transistors MN20 and MN21, the gate width is set to a minimum allowable value to minimize the OFF drain current, and the channel length thereof is set to a value greater than the minimum allowable value to reduce the short channel effect. MN20 functions as the first charging transistor, and MN21 functions as the second charging transistor. More specifically, NMOSFETs with a gate length of 0.8 μm and a gate width of 0.5 μm were used. Furthermore, to prevent the transistors from having too great an internal electric field, the gate oxide was formed so as to have a relatively large thickness (5 nm), and the impurity concentration of the substrate was optimized. As a result, the OFF drain current was smaller than 10 fA even if a maximum variation occurs. To expand the input range of the differential amplifier, the ratio of the gate width to the gate length was set to be large for NMOSFETs MN22 and MN23. MN22, MN23, and MN24 function as the first differential amplifier or as the fourth differential amplifier. More specifically, in the present example, the gate width was set to 40 μm and the channel length was set to 1 μm. The gate width of MN24 was set to be 4 times greater than that of MN11 so that a current of 120 μA, which was 4 times greater than that of MN11, was obtained.

Figure 17:
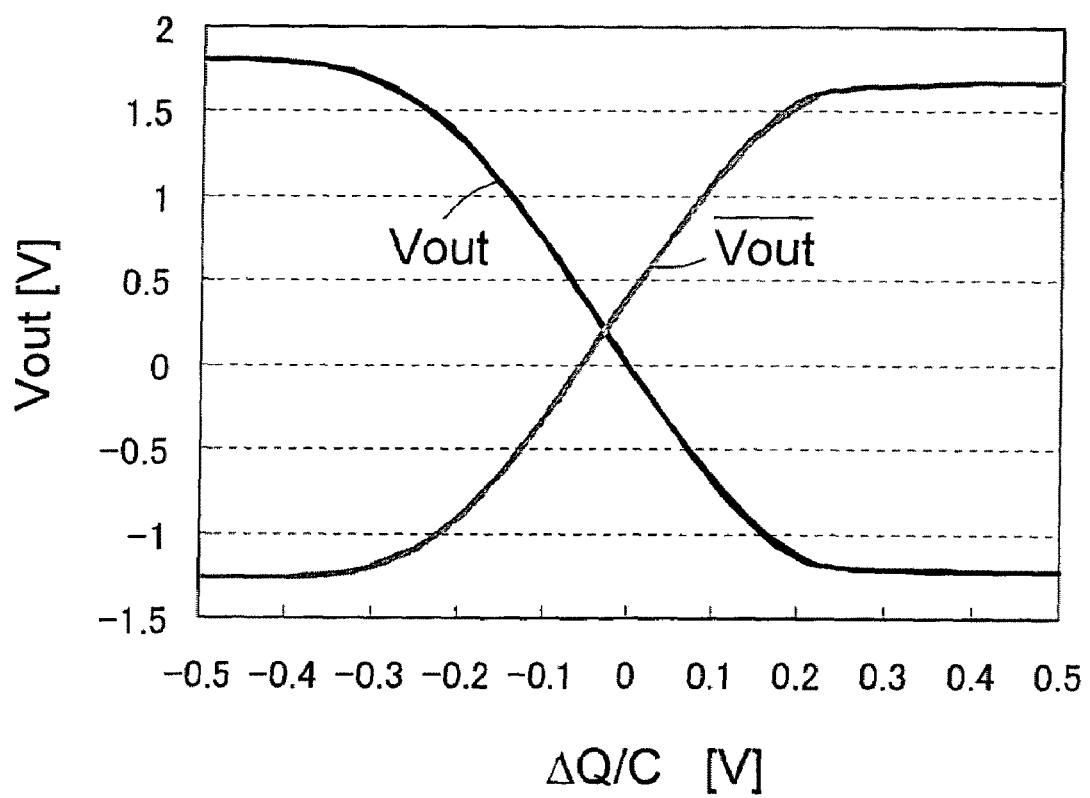
FIG. 17 is a characteristic diagram illustrating operating waveforms of the circuit shown in FIG. 16.

More specifically, the gate width of MN24 was set to 40 μm, and the gate length thereof was set to 1 μm. Furthermore, parameters were designed so that VDD−VSS=4.2 V appears across the resistors R5 and R6. More specifically, for the current equal to 120 μA, the resistance of the R5 and R6 was set to 30 kΩ. For MN25, MN26, MN27, and MN28, the gate width was set to 10 μm and the channel length was set to 1 μm. FIG. 17 illustrates output characteristics. A horizontal axis indicates DQ/C, i.e., the ratio of a change in charge DQ in the solution on the electrode of ISFETb to capacitance C between the charge and the reference electrode. As shown in FIG. 17, a change in potential caused by a charge in the solution was amplified by a factor of about 10. It is possible to detect a change in charge DQ in a range of DQ/C from +0.2 V to −0.2 V. In the present example, the parameters were designed based on the fact that the difference in charge DQ/C between a state in which there is DNA with a double helix and a state in which there is no DNA with a double helix is about 0.15 V. Note that the charge detection range can be adjusted by the ratio of the gate width to the gate length and the current.

(Overall Circuit of Detection Apparatus)

Figure 18:
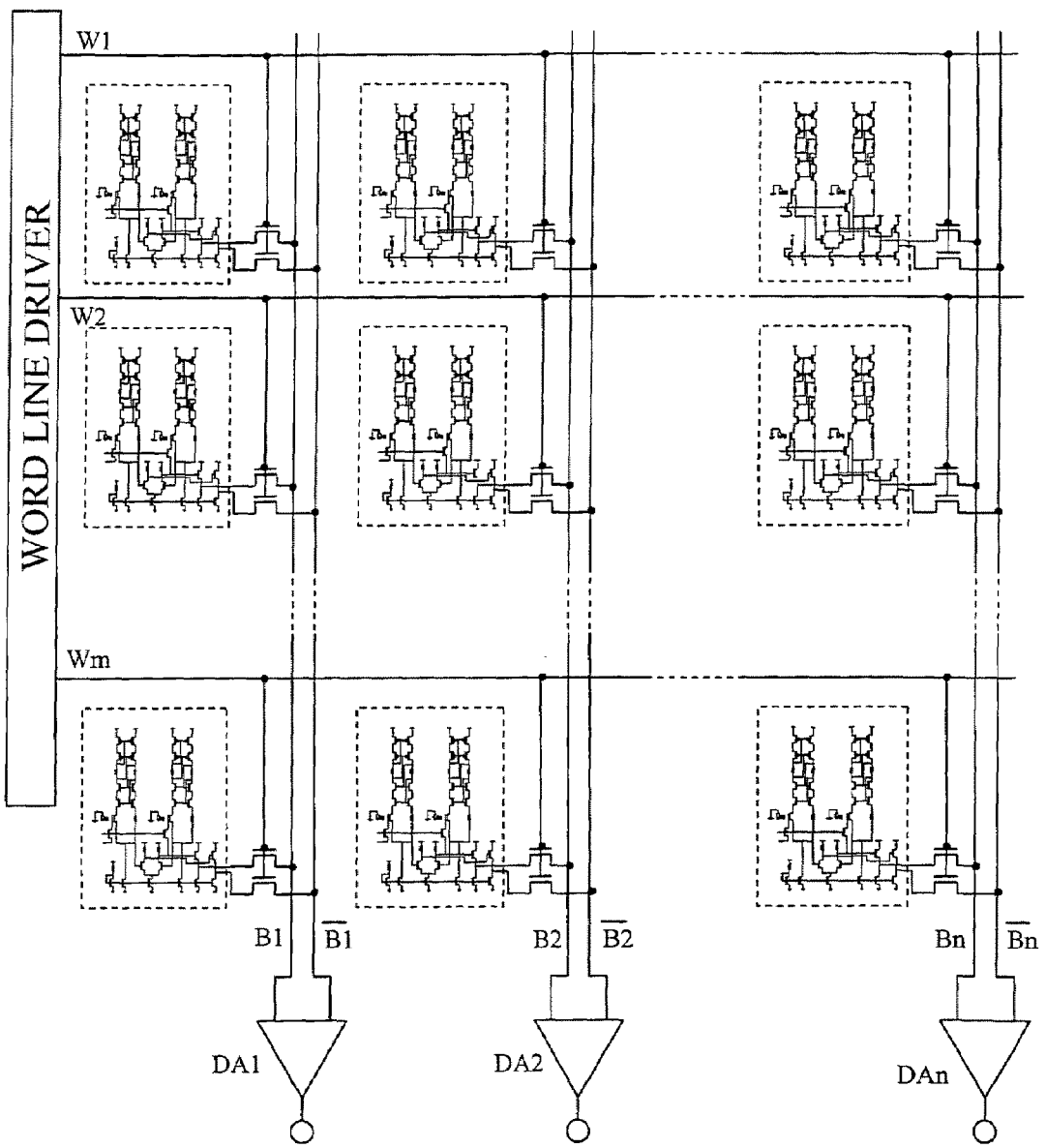
FIG. 18 is a circuit diagram illustrating a detection apparatus configured by disposing circuits, each similar to the circuit shown in FIG. 16, in the form of a matrix array according to the second embodiment of the present invention.
Figure 19:
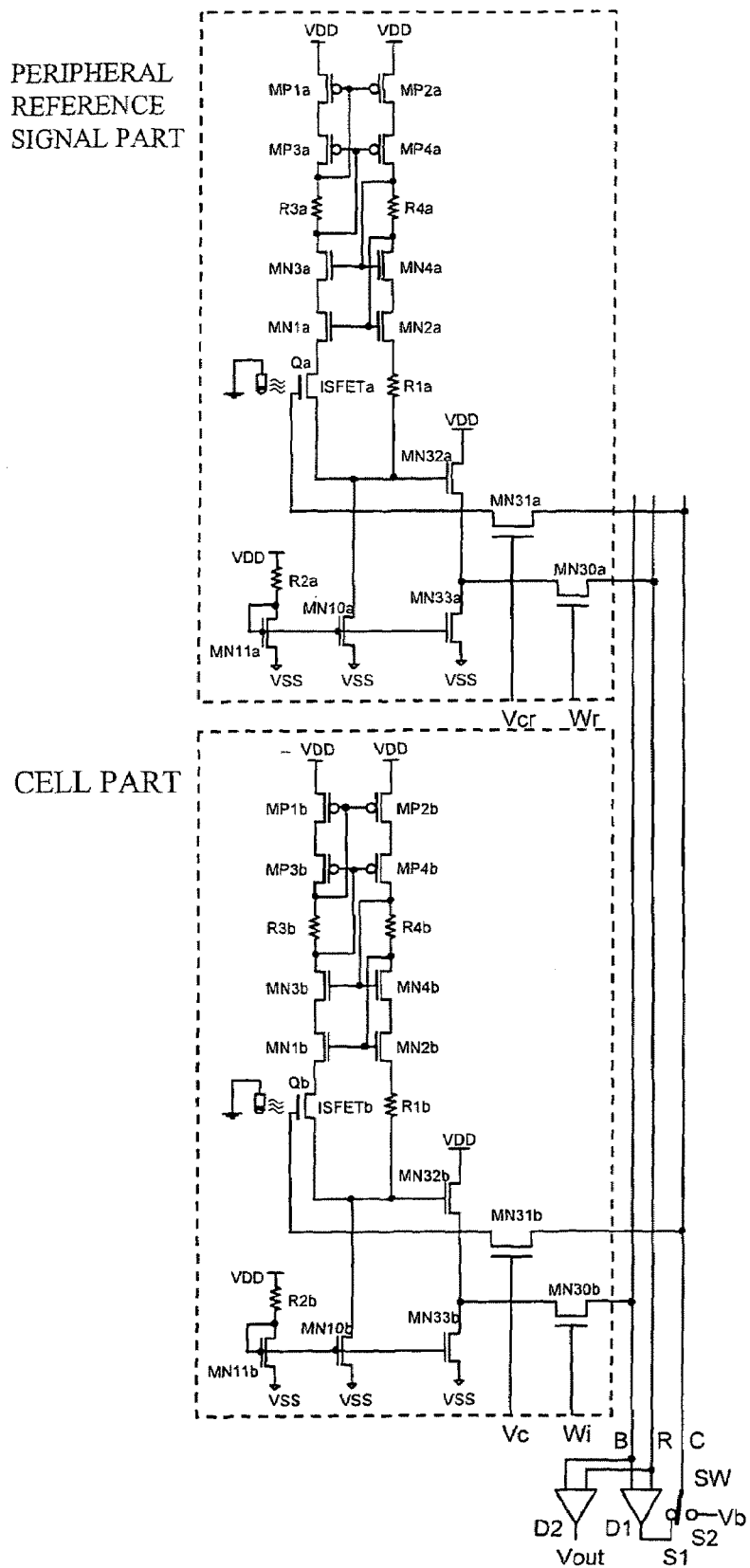
FIG. 19 is a diagram illustrating another example of a detection apparatus according to the second embodiment of the present invention.

FIG. 18 illustrates a device obtained by disposing circuits, each similar to the circuit shown in FIG. 16, in the form of a matrix array. Complementary outputs are amplified by differential amplifiers DA1, DA2, . . . , DAn located in a peripheral area and output to the outside. In FIG. 18, two ISFETs are disposed in each cell. If reference ISFETs are disposed in a peripheral area of the cell array, it is possible to reduce the cell area to about ½. To achieve this, as shown in FIG. 19, the circuit shown in FIG. 15 is separated into a cell part and a peripheral reference signal part, and source followers MN32a, MN33a, MN32b, and MN33b functioning as output transistors are added to increase the ability to drive bit lines. The cell part and the peripheral reference signal part are similar in circuit configuration although there is a difference in connection to a bit line B and a reference line R. The differential amplifier functioning as the fourth differential amplifier is disposed in the peripheral area. In the present example, two differential amplifiers, i.e., a compensation differential amplifier D1 and an output differential amplifier D2 are provided, and gains thereof are optimized. These differential amplifiers D1 and D2 function as the fourth differential amplifier.

The operation of the circuit shown in FIG. 19 is described in further detail below. In an initial state, an OFF gate voltage (for example, VSS) is applied to Wr, Wi, Vcr, and Vc, and thus transistors MN30a, MN30b, MN31a, and MN31b are in the OFF state. MN30a and MN30b function as the pass gate transistors, and MN31a and MN31b function as the first charging transistor and the second charging transistor, respectively. First, setting is performed as to the compensation charge Qa on the gate electrode of the reference field effect transistor ISFETa in the peripheral reference signal part. To perform this setting, the switch SW is switched to a side S2 to set the voltage on the calibration line C to Vb, and then the ON gate voltage (for example, VDD) is applied to Vcr thereby to apply Vb to the gate electrode of ISFETa. Subsequently, the OFF gate voltage is applied to Vcr. Thereafter, setting is performed as to the compensation charge Qb on the gate electrode of the charge detection field effect transistor ISFETb in the cell part. That is, the switch SW is switched to a side S1 and the ON voltage is applied to Wr, Wi, and Vc. As a result, the charge Qb on the gate electrode of ISFETb in the cell part is determined so that the voltage of the bit line B becomes equal to the voltage of the reference line R. The OFF gate voltage is then applied to Vc to complete the compensation process. Thereafter, a detection process is performed. In the detection process, the switch SW is switched to the side S2 applied with Vb and is maintained in this state. This makes it possible to reduce noise from the calibration line C and reduce the drain-source voltage of MN31a and MN31b, which results in a reduction in the OFF current which results in an increase in retention time of Qa and Qb.

Note that the differential amplifiers D1 and D2 may be replaced with a single differential amplifier, and this single differential amplifier may be shared in the operation.

To attract or remove a charged substance (for example, DNA) to or from the metal electrode, it is effective to apply a voltage to the gate electrode of ISFET. To perform this, after the OFF gate voltage is applied to Wr and Wi, a proper voltage is applied to Vb and the switch SW is switched to the side S2. By applying the ON gate voltage to Vcr and Vc, it is possible to apply the voltage of Vb to the gate electrode of ISFETa and ISFETb. This is effective, in particular, to fix the probe DNA on the gate electrode and to remove the target DNA remaining on the gate electrode without forming a double helix.

Figure 20:
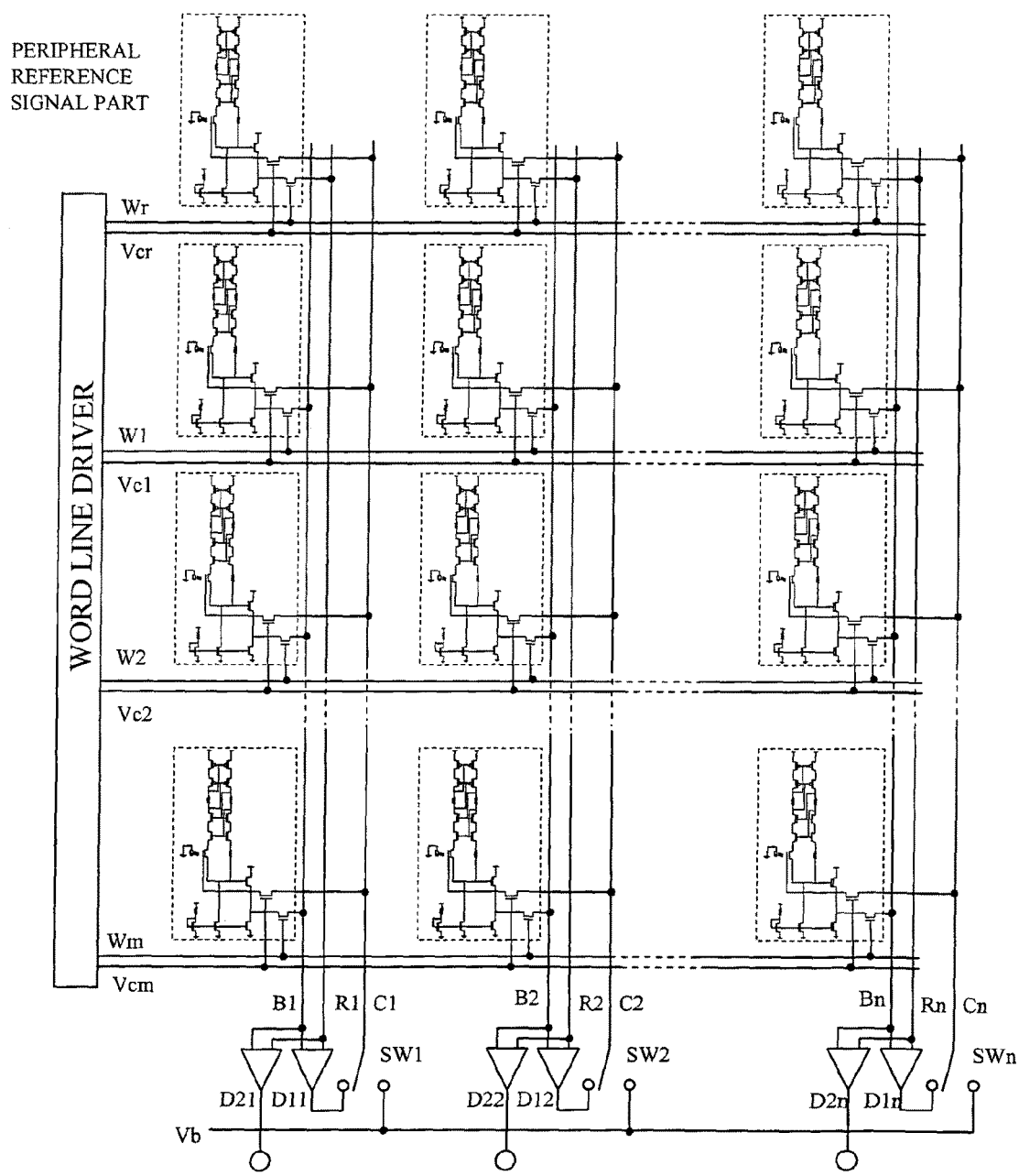
FIG. 20 is a circuit diagram of a detection apparatus configured by disposing circuits, each similar to the circuit shown in FIG. 19, in the form of a matrix array.

FIG. 20 illustrates a device obtained by disposing circuits, each similar to the circuit shown in FIG. 19, in the form of a matrix array. A reference signal is shared by each column, and thus each cell has an area nearly equal to that shown in FIG. 10.

Embodiment 3

In this embodiment, resistors (R1 to R4) in the previous embodiments are all replaced with transistors.

Figure 21:
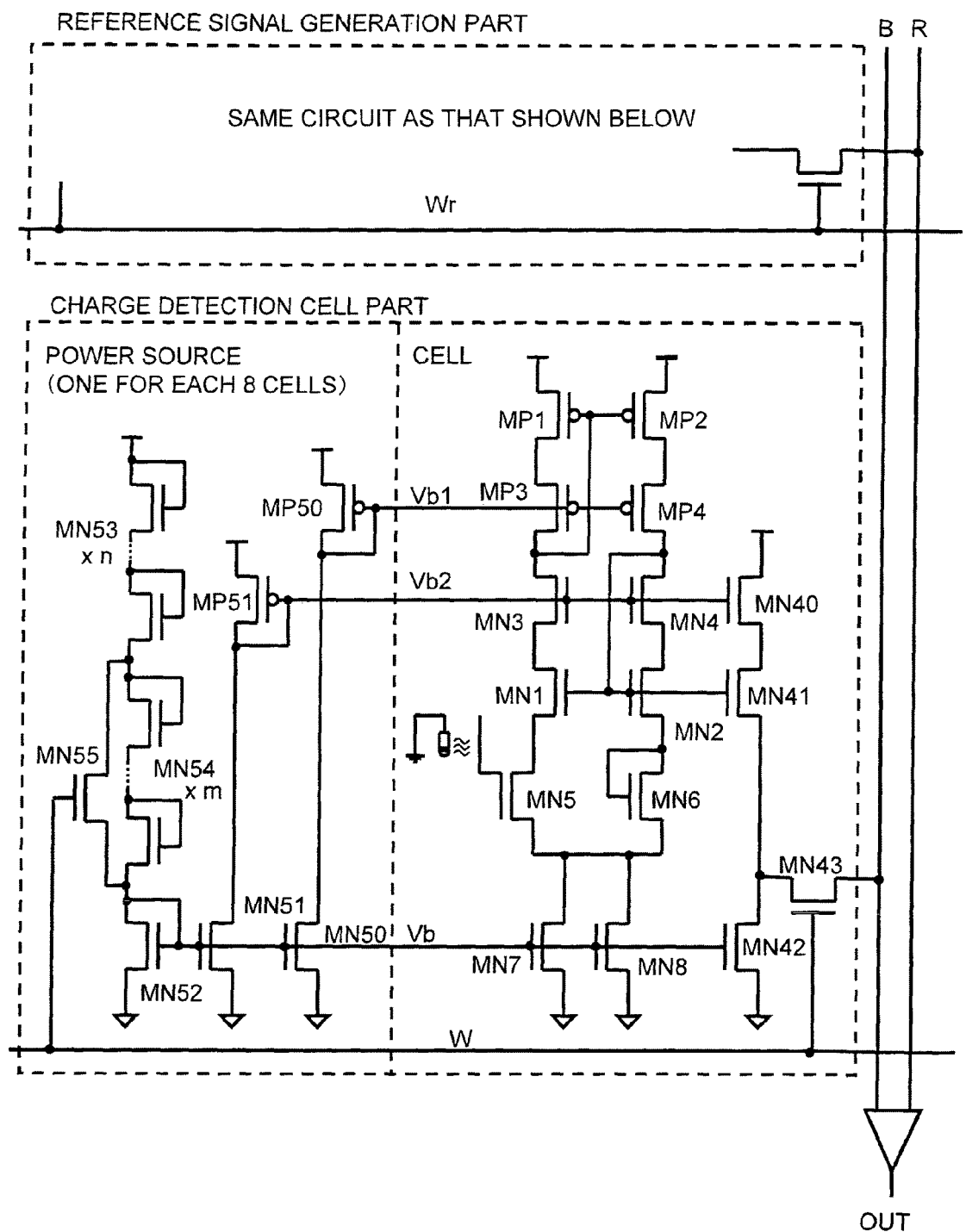
FIG. 21 is a diagram illustrating a circuit of a detection apparatus according to a third embodiment of the present invention.

To achieve a DNA chip capable of performing genome analysis with a high throughput, it is necessary to integrate one million or more cells each including a charge detection transistor and a control part on the chip. To meet this requirement, it is necessary to reduce the cell size and reduce the power consumption of each cell. To reduce the cell size, it is effective to use transistors or diodes instead of the resistors (R1 to R4). The gate that is to be brought into contact with biomolecules is formed in an extension gate structure extending over the charge detection transistor and the control circuit. A specific example of this configuration is shown in FIG. 21.

MP1 to MP4 and MN1 to MN4 are similar to those shown in FIG. 4B. The gate voltage of MN1 and MN2 is received by a cascode-connection source follower circuit including MN40, MN41, and MN42, and an output signal thereof is selectively transferred over a bit line B via a pass gate transistor MN43. The series connection of MN40, MN41, and MN42 functions as the second output circuit. In the reference signal generation part, there is provided a first output circuit composed of a series connection of transistors connected to the reference field effect transistor in a similar manner to the above-described series connection of MN40, MN41, and MN42 functioning as the second output circuit. By forming a pair of MN5 and MN6, a set of MN1, MN2, and MN41, and a set of MN3, MN4, and MN40 such that the transistors have the same layout and the same orientation within each pair or set and the transistors are located close to each other within each pair or set, it becomes possible for the voltage of the extension gate of the charge detection transistor MN5 to directly appear on the bit line, and thus it becomes possible to achieve an output that substantially does not depend on the cell-to-cell variation in threshold value of transistors, the substrate bias effect, the variation in the power supply voltage, and the variation in temperature. In this configuration, because it becomes possible to neglect the cell-to-cell variation in threshold value of transistors, the substrate bias effect, the variation in the power supply voltage, and the variation in temperature, the detection signal and the reference signal have a sufficiently close value without having to perform the initialization of the charge on the gate electrode, and thus it is possible to deal with the difference signal without initialization of the charge on the gate electrode. Therefore, the gate electrode does not need to be connected with the charging transistor, and the gate electrode is allowed to be in the floating state from the beginning. This is advantageous to retain the charge on the gate electrode. Note that the variation in the initial amount of charge on the gate electrode still remains. To reduce this variation, it is effective to perform initialization by ultraviolet ray irradiation.

In a power source part, Vb1 is generated by MP50 and MN50, and Vb2 is generated by MP51 and MN51, and furthermore Vb is given by MN52, MN53, MN54, and MN55. The gate width to channel length ratio of MP50 is set to be ¼ of that of MP3 and MP4, and a gate overdrive voltage is set to be twice that for MP3 and MP4. MN53 is composed of a series connection of n transistors, and MN54 is composed of a series connection of m transistors. When a row is selected (when W is high), a voltage equal to (VDD−VSS)/(n+1) is applied to Vb, while when no row is selected (when W is low), a voltage equal to (VDD−VSS)/(m+n+1) is applied to Vb. This allows a reduction in power consumption in a waiting state, while maintaining capability of outputting a stable signal voltage in a reading process and also maintaining high ability to drive the bit line. This bias circuit is provided such that one circuit is disposed in the center of each eight cells. This allows a reduction in a variation in voltage on power supply lines and a reduction in influence of noise, and it also becomes possible to reduce the power consumption and the total size.

In the present embodiment, specific parameter values were set as follows. That is, VDD=3V, VSS=0V, the gate width=4 μm and the channel length=1 μm for MP1, MP2, MP3, MP4, and MP51, the gate width=1 μm and the channel length=1 μm for MP50, and the gate width=2 μm and the channel length=1 μm for all NMOSFETs. MN53 is given by a series connection of 4 transistors (n=4), and MN54 is given by a series connection of 4 transistors (m=4). The cell size was set to 30 μm×30 μm. The power consumption per cell in the non-selection state was 0.07 μW. The total chip size including an array of one million cells was 4 mm×4 mm, and the total power consumption was 100 mW.

Figure 22:
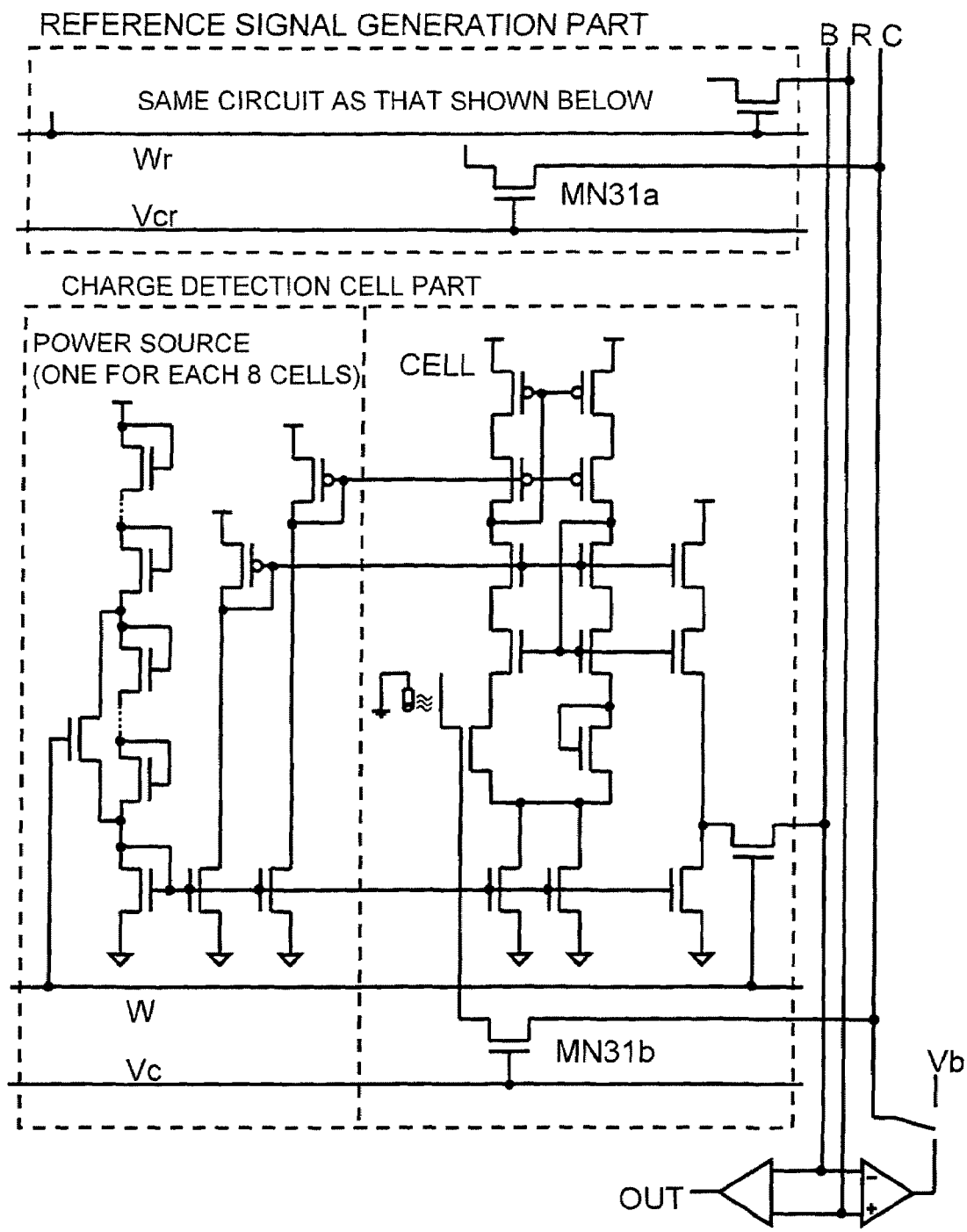
FIG. 22 is a diagram illustrating another configuration of a detection apparatus according to the third embodiment of the present invention.

FIG. 22 illustrates an example in which a transistor MN31b is connected to the extension gate of the charge detection transistor MN5 thereby to control the amount of charge on the extension gate. The total configuration is similar to that shown in FIG. 20.

Figure 23A:
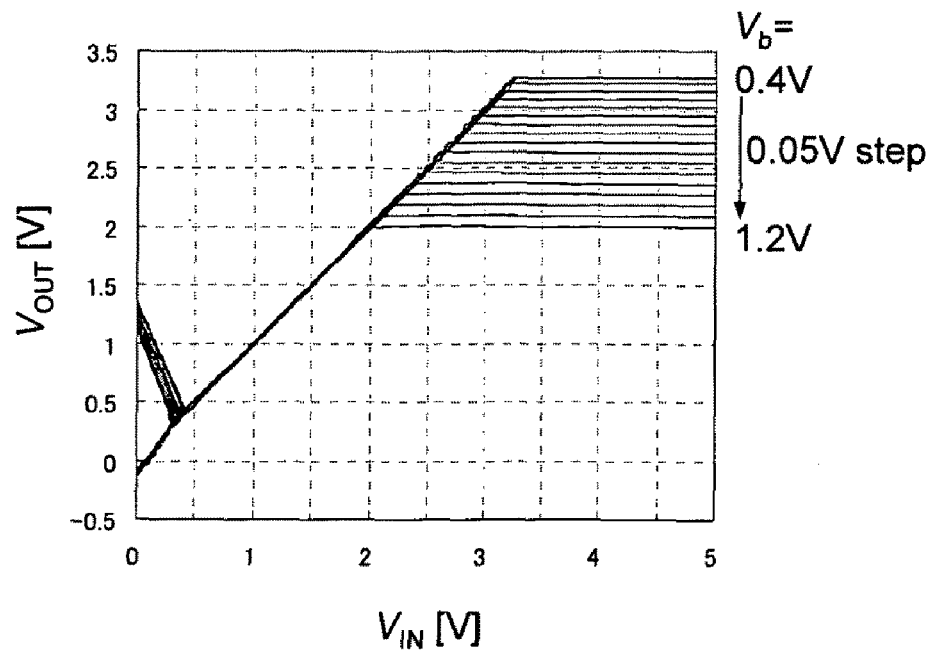
FIG. 23A is a characteristic diagram illustrating a measurement result of an input-output characteristic of the detection apparatus shown in FIG. 21 according to the third embodiment.
Figure 23B:
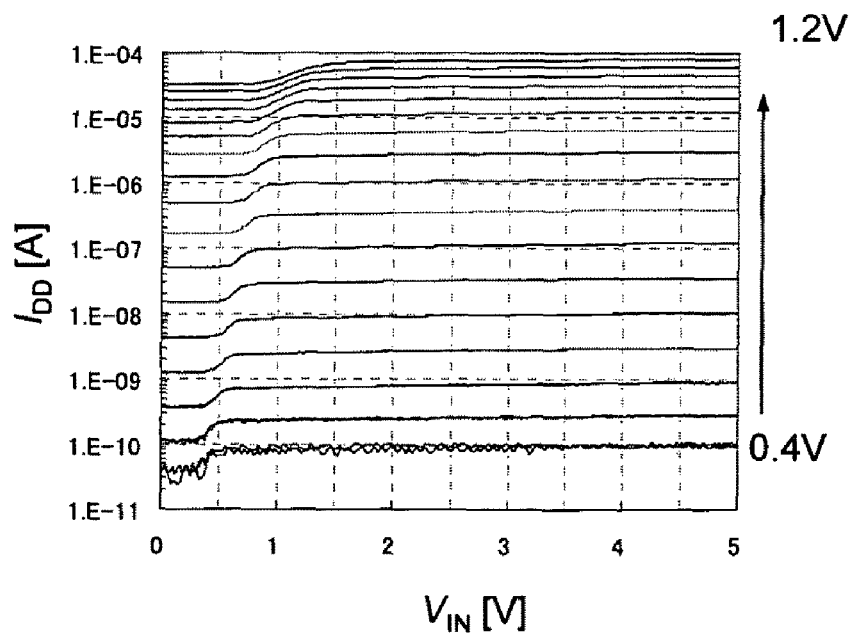
FIG. 23B is a characteristic diagram illustrating a measurement result of an input voltage vs. total drain current characteristic of the detection apparatus shown in FIG. 21 according to the third embodiment.

Characteristics of the detection apparatus shown in FIG. 21 were measured. Measurement results are shown in FIG. 23A and FIG. 23B. FIG. 23A illustrates the input-output characteristic of the detection apparatus. A horizontal axis $V_{IN}$ indicates a voltage applied to the extension gate of the ISFET MN5, and a vertical axis $V_{OUT}$ indicates an output voltage on the bit line B. A parameter $V_b$ is a voltage applied to the gate of MN7, MN8, etc. The parameter $V_b$ was varied in steps of 0.05 V over the range from 0.4 to 1.2 V. The applied power voltages were set such that VDD=5 V and VSS=0 V. When $V_b$ was 0.4 V, as can be seen, the output voltage $V_{OUT}$ changed in proportion to the input voltage over the range of input voltage $V_{IN}$ from 0.4 V to 3.2 V. In the present embodiment, as can be seen, the output voltage $V_{OUT}$ obtained was equal to the input voltage $V_{IN}$. When $V_b$ was 1.2 V, as can be seen, the output voltage $V_{OUT}$ changed in proportion to the input voltage over the range of input voltage $V_{IN}$ from 0.4 V to 2 V.

FIG. 23B illustrates the total drain current $I_{DD}$ of the charge detection cell (the sum of currents flowing through MN7, MN8, MN42, MN50, and MN51) vs. the gate voltage $V_{IN}$ of MN5. It can be seen that the normal operation was achieved over the range of the total drain current $I_{DD}$ from 100 pA to 100 μA. The consumption power was 500 pW to 500 μW.

Figure 24:
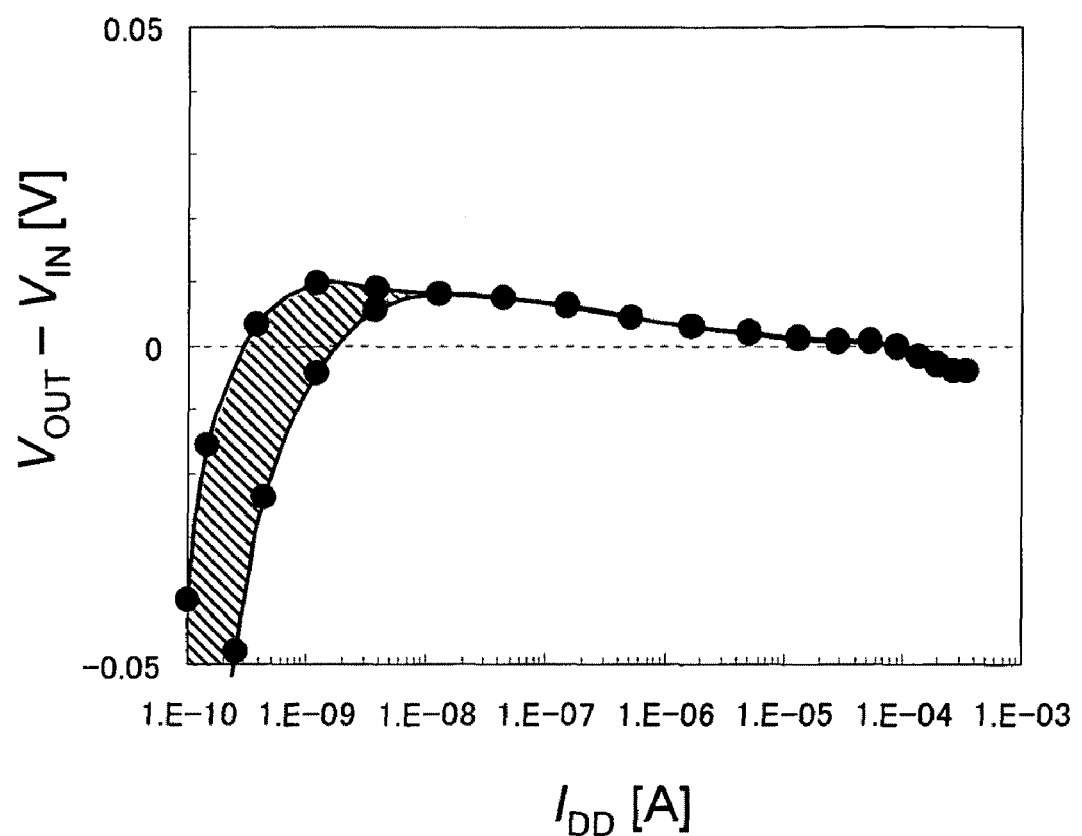
FIG. 24 is a characteristic diagram illustrating a measurement result of the characteristic of the detection apparatus shown in FIG. 21 according to the third embodiment, in terms of the difference between output and input of the detection apparatus as a function of the total drain current.

FIG. 24 illustrates the relationship of the total drain current $I_{DD}$ with the difference (error) between the output voltage $V_{OUT}$ and the input voltage $V_{IN}$. When the total drain current $I_{DD}$ was equal to or smaller than 10 nA, the output $V_{OUT}$ showed hysteresis. However, when the total drain current $I_{DD}$ was greater than 10 nA and the consumption power was greater than 50 nW, the error was in the range of 0.0080 to −0.0040 V.

Figure 25:
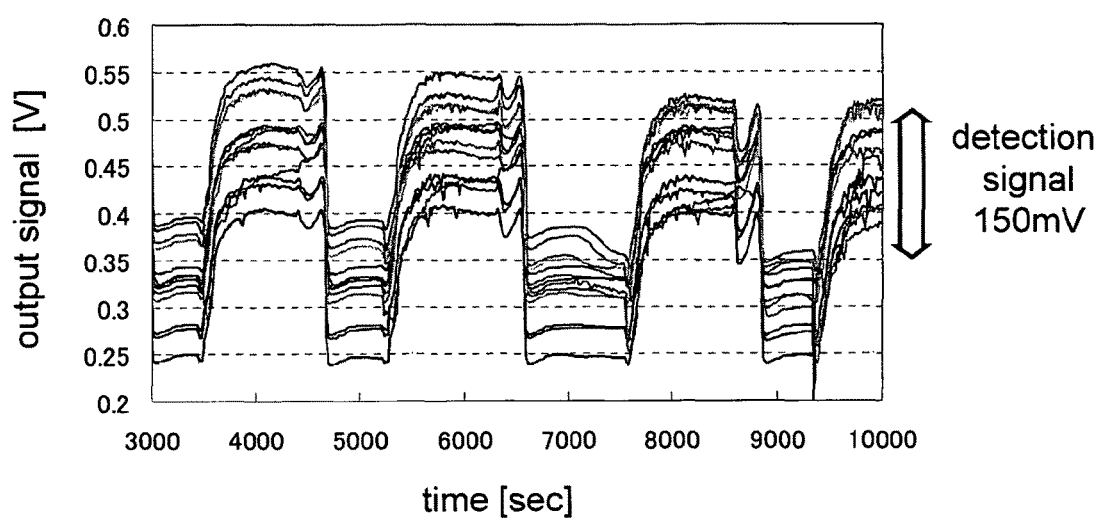
FIG. 25 is a characteristic diagram illustrating a measurement result of the characteristic of the detection apparatus shown in FIG. 21 according to the third embodiment, in terms of a change in output with time that occurs when pure water and phosphate buffer solution are alternately supplied to a chip.

Thereafter, in the detection apparatus shown in FIG. 21, pure water and a phosphate buffer solution were alternately supplied to the chip, and the sensitivity to the ion concentration was measured. The result is shown in FIG. 25. The signals from the respective cells arrayed in the form of a matrix had substantially the same shape.

Figure 26:
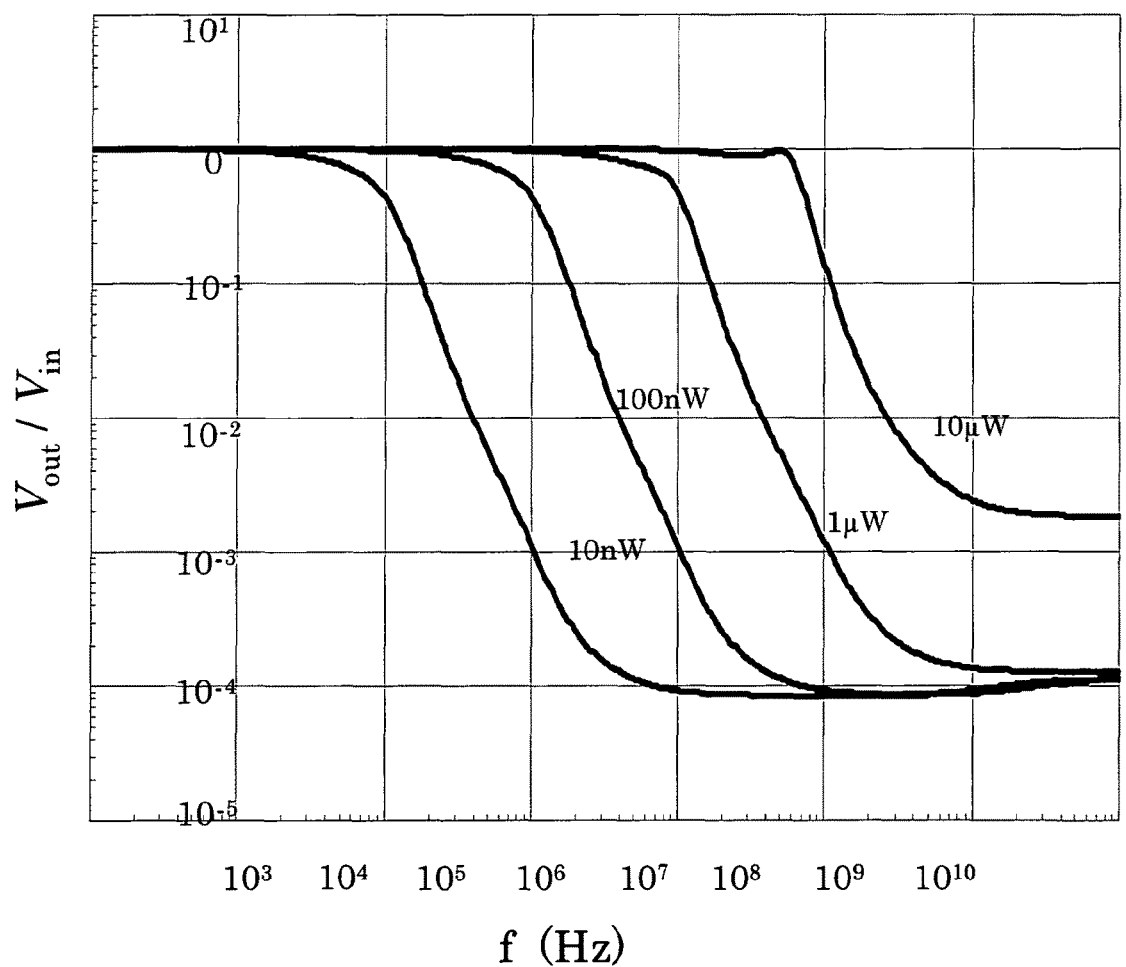
FIG. 26 is a characteristic diagram illustrating a measurement result of a frequency response characteristic of the detection apparatus shown in FIG. 21 according to the third embodiment.

Thereafter, the frequency response characteristic of the detection apparatus shown in FIG. 21 was measured as shown in FIG. 26. The vertical axis indicates log($V_{OUT}/V_N$) in FIG. 26. The consumption power was used as a parameter, and the measurement was performed for 10 nW, 100 nW, 1 μW, and 10 μW. As can be seen from this figure, the response speed increased with the consumption power. If the detection apparatus is operated with consumption power of 1 μW, it is possible to read the cell signal at as high a speed as a few μsec. In the waiting state, if the consumption power is set to 10 nW, which is the lowest power that allows the ISFET to be maintained at a fixed operating point, it is possible to reduce the overall consumption power of the apparatus.

Figure 27:
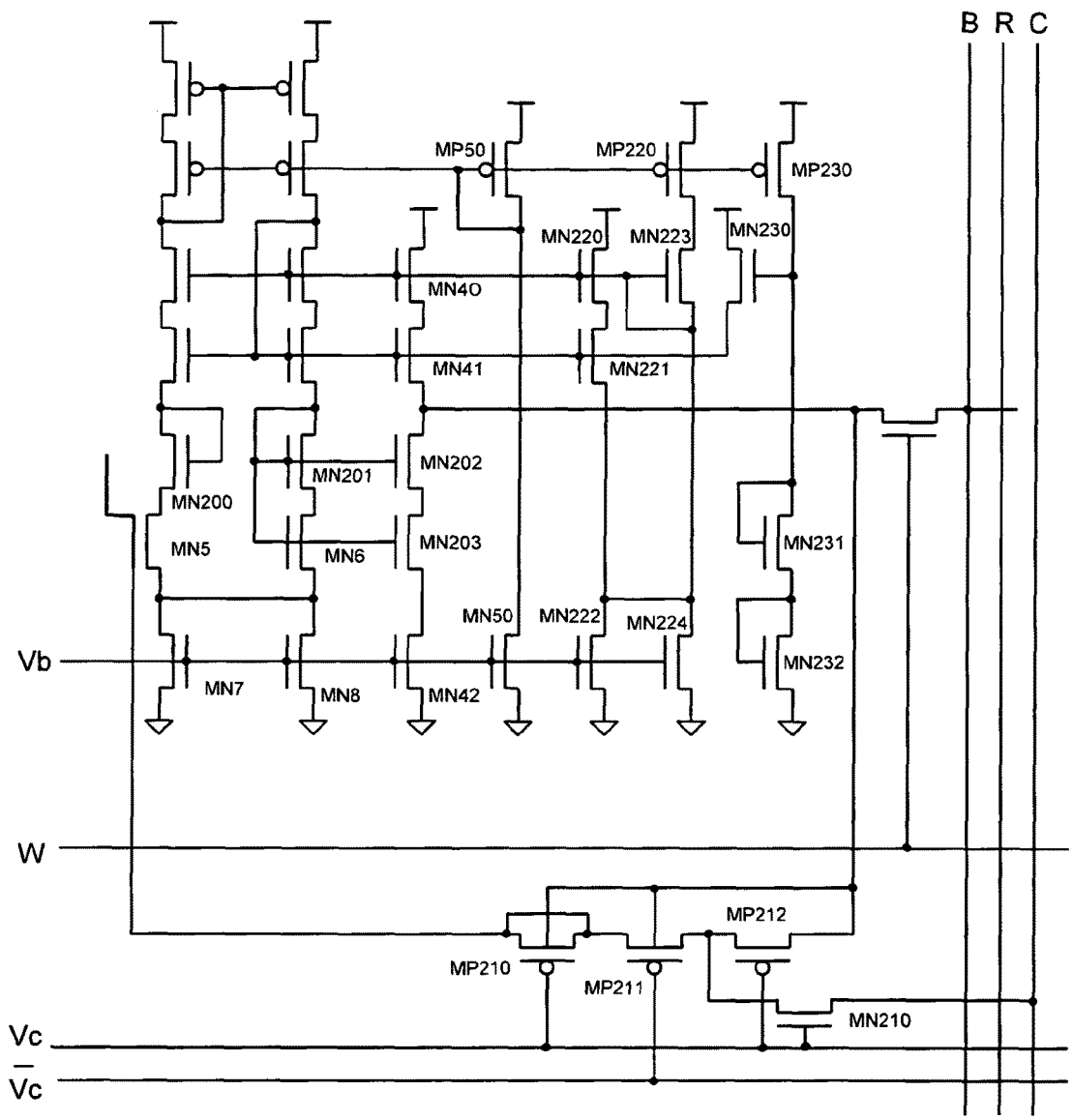
FIG. 27 is a circuit diagram illustrating an improved configuration of the detection apparatus shown in FIG. 22 according to the third embodiment of the present invention.

FIG. 27 illustrates an example of an improvement of the detection apparatus shown in FIG. 22. A diode-connected MN200 is inserted at the drain of MN5, and MN201 is inserted at the drain of the diode-connected MN6. Note that the gate of MN6 is connected to the gate of MN201. At the source of MN41, cascode-connected MN202 and MN203 whose gates are respectively connected to the gates of MN201 and MN6 is inserted. MN200, MN201, and MN202 are transistors that are equal in size and that have a smaller gate width to gate length ratio than that of MN5 and have a large gate overdrive voltage. The difference between the overdrive voltage of MN5 and the overdrive voltage of MN200, MN201, and MN202 is given as the source-drain voltage of MN5. MN203 is a transistor provided for allowing the source voltage of MN202 to be equal to the source voltage of MN201 thereby reducing the error caused by the channel length modulation effect and thus achieving higher accuracy in the output voltage. As described above, by providing MN200, MN201, and MN202, the source-drain voltage of the ISFET MN5 is reduced thereby achieving high stability in operation. By the series connection of MN40, MN41, NM202, and MN203, the drain voltage of MN202 is made equal to the gate voltage of the ISFET, and the output signal of the detection apparatus is given by this drain voltage of MN202. The series connection of MN40, MN41, NM202, and MN203 functions as the second output circuit. Similarly, in the reference signal generation part, there is provided a first output circuit composed of a series connection of transistors connected to the reference field effect transistor in a similar manner to the above-described series connection of MN40, MN41, NM202, and MN203 functioning as the second output circuit associated with the ISFET.

There is provided a circuit for supplying bias voltage to the extension gate of MN5. This part for supplying bias voltage to the gate corresponds to the bias supply system of the circuit shown in FIG. 19. This part is configured in a similar manner to that shown in FIG. 19 so that the same charge is supplied also to the gate of the ISFET in the reference signal part. In this bias supply circuit, MN210 and MP211 are transistors for applying a voltage to the gate of MN5 from the calibration line C, and these transistors corresponds to MN31b in FIG. 19. MN210 and MP211 function as the second charging transistors. In parallel to MN210, MP212 with a source connected to the drain of MN202 is disposed. MP212 is for reducing the leakage current of MP211 by making the source-drain voltage of MP211 nearly equal to 0 V when MP211 is in the OFF state. MP210 is connected between the gate of MN5 and the source of MP211. MP210 and MP211 function as switches that prevent a charge from injecting into the extension gate of MN5 from the channel of MP211 when MP211 is switched from the ON state into the OFF state. MP211 is implemented by a parallel connection of two transistors with the same size as that of MP210.

It turns out that when the bias circuit for providing Vb2 in FIG. 21 is used, the input voltage range is small. To improve this, a bias circuit shown in FIG. 27 is employed instead of MP51 and MN51 in FIG. 21. This bias circuit includes a parallel connection of two series connection circuits one of which includes MN220, MN221 with a drain connected to the source of MN220, and MN222 with a drain connected to the source of MN221, and the other one of which includes MN223, MN224 with a drain connected to the source of MN223, and MP220 with a drain connected to the drain of MN223. The drain of MN222 and the drain of MN224 are connected to each other, and the gate and the source of MN223 are connected to each other. The gate of MN220 and the gate of MN223 are connected to the gate of MN40, and the gate of MN221 is connected to the gate of MN41. MN220 is a transistor with the same size as MN40. MN223 is a transistor with a gate width to gate length ratio smaller than that of MN40 and having a large gate overdrive voltage. MN221 is a transistor with the same size as MN41. MN222 and MN224 are transistors with the same size as MN50. MP220 is a transistor with the same size as MP50. By using this bias circuit, it is possible to increase the input voltage range from 2 V to 3.5 V and reduce the error from 10 mV to 1 mV.

When the voltage of the extension gate is low, all transistors are turned off, and it takes a long time to get out of this state.

Furthermore, because the output node is brought into a high-impedance state, there can occur a problem that a large load capacitor connected to the bit line causes the output voltage to be fixed at a particular value. To improve this, there is provided a second startup circuit including a series connection of MN230 with a source connected to the gate of MN221, MP230 with a drain connected to the gate of MN230, MN231 with a drain connected to the drain of MP230 and also connected to the gate of MN230, and MN232 with a drain connected to the source of MN231. The gate and the drain of MN231 are connected to each other, the gate and the drain of MN232 are connected to each other, and the gate of MP230, the gate of MP220, and the gate of MP50 are connected together. This startup circuit operates only when the input voltage becomes low and, as a result, all transistors are brought into the off state. The startup circuit prevents the gate voltage of MN41 and MN221 from becoming lower than the threshold value of the transistors, thereby allowing a current to always flow and thus preventing the output node from being brought into the high-impedance state. Note that, in the reference signal generation part, there is provided a first startup circuit including a series connection circuit having the same circuit configuration as that of the second startup circuit described above.

Figure 28:
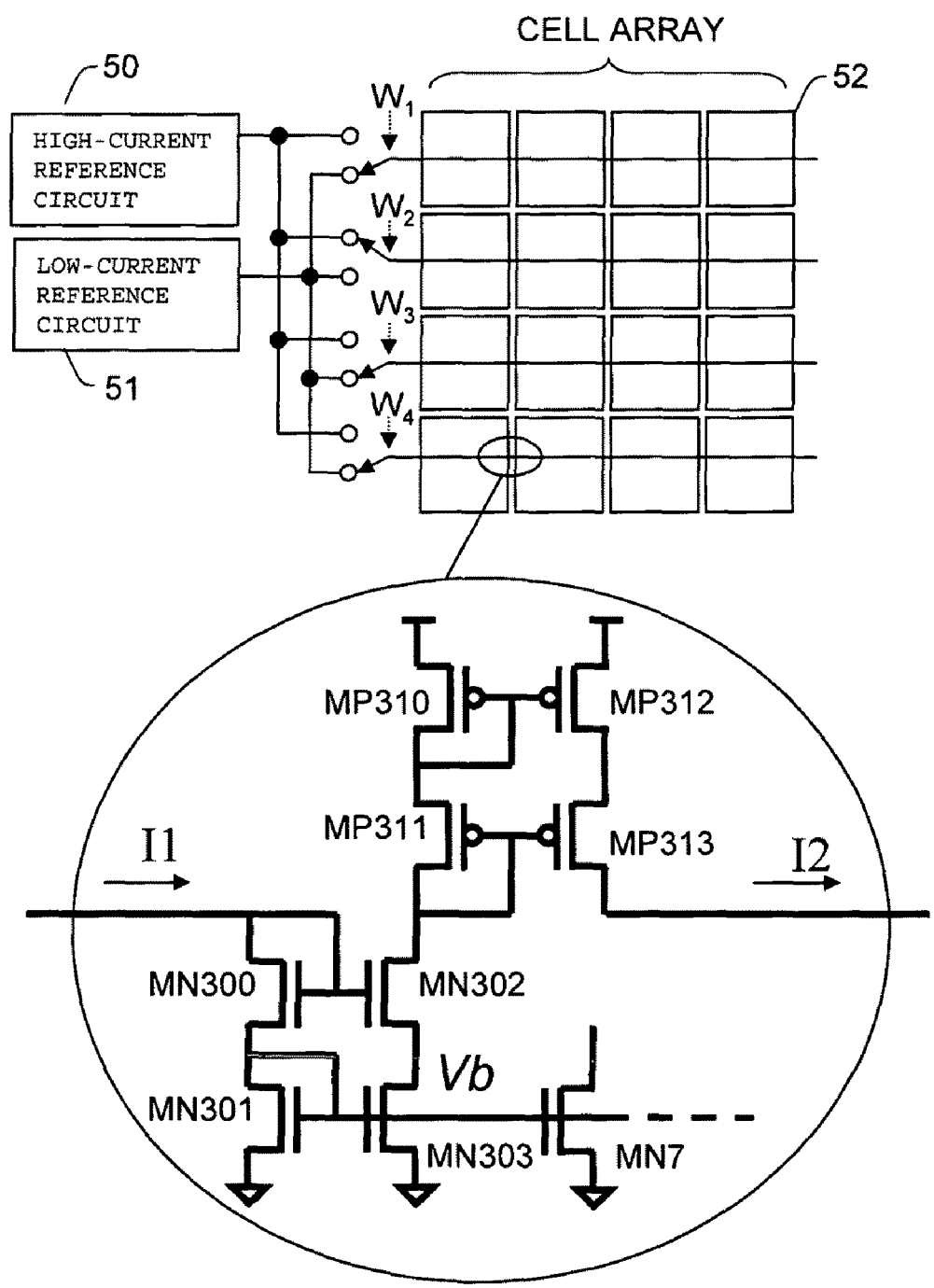
FIG. 28 is a circuit diagram illustrating a configuration of a bias circuit of the detection apparatus shown in FIG. 27.

It also turns out that in the circuit shown in FIG. 21, the bias circuit including MN52, MN53, MN54, and MN55 for providing Vb is not very good in temperature characteristic. To improve this, a circuit configuration shown in FIG. 28 may be used. In this configuration, current reference circuits 50 and 51 are provided outside the cell array 52. Furthermore, there is provided a first current mirror circuit including a first series connection circuit and a second series connection circuit, the first series connection circuit including MP310 and MP311 disposed in a cell, the second series connection circuit includes MP312 and MP313 disposed in an adjacent cell. In the former cell, there is provided a third series connection circuit including MN302 and MN303 and connected to the first series connection circuit and there is further provided a fourth series connection circuit including MN300 and MN301 configured so as to form a current mirror with respect to a current flowing through the third series connection circuit. That is, a second current mirror circuit is formed by the third series connection circuit and the fourth series connection circuit. The gate and the drain of MN300 are connected to each other, and the gate and the drain of MN301 are also connected to each other. The gate and the drain of MP310 are connected to each other, and the gate and the drain of MP311 are also connected to each other. A reference current I1 is supplied to the drain of MN300, and a drain current I2 of MP313 is supplied to the drain of MN300 in the adjacent cell. In this way, the reference current I1 is supplied to the leftmost cell in each row via changeover switches W1 to W4 from the high-current reference circuit 50 and the low-current reference circuit 51. By the operation of the current mirror circuit, I1=I2, and thus the current supplied to any cell from the reference circuits 50 and 51 is equal in magnitude. Thus, the drain voltage of MN301 is supplied as the bias voltage Vb to MN7, MN8, MN42, etc., in each cell. In this way, cells are connected via current mirrors thereby the temperature-independent current I is supplied from the high-current reference circuit 50 or the low-current reference circuit 51 thereby making it possible to achieve high-stability operation over a wide temperature range. The high-current reference circuit 50 supplies a high current of 1 μA, and the low-current reference circuit 51 supplies a low current of 1 nA. When a detection signal is read, the current is switched to the high current to make it possible to read the detection signal at a high speed. In the waiting state, the current is switched to the low current to reduce the consumption power while protecting the ISFET.

Figure 29:
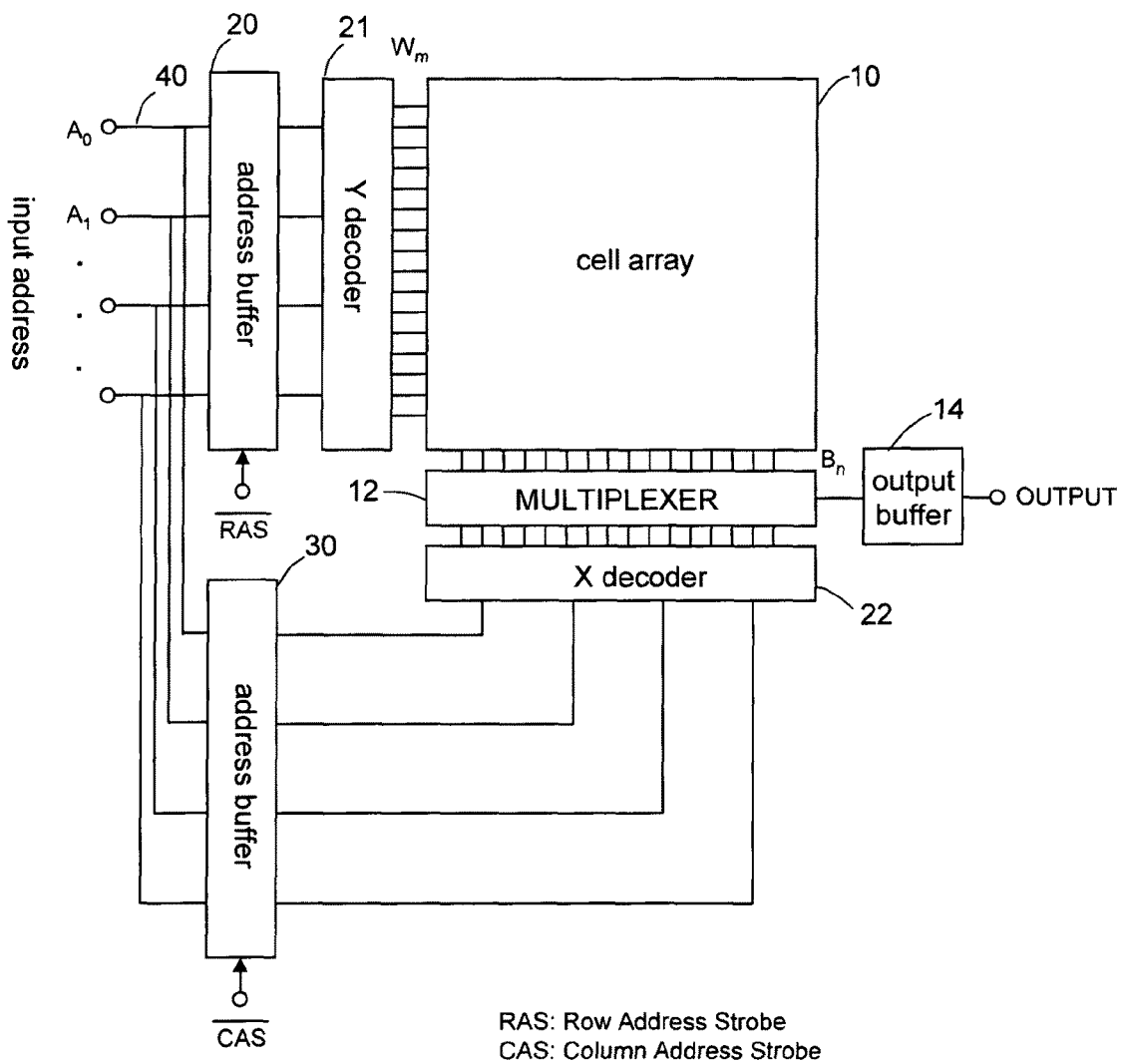
FIG. 29 is a diagram illustrating a circuit of reading each cell in the detection apparatus shown in FIG. 22 according to the third embodiment.

FIG. 29 illustrates a circuit for accessing each cell in the detection apparatus shown in FIG. 27. A row address and a column address are input in a time-sharing manner via address lines 40. The row address data is stored in an address buffer 20 in synchronization with a RAS signal, and the column address data is stored in an address buffer 30 in synchronization with a CAS signal. The row address data is converted by a Y decoder 21 into a Y coordinate of a cell array 10, and the column address data is converted by an X decoder 22 into an X coordinate. If the Y coordinate is given, then, as shown in FIG. 20, data existing in a row specified by the Y coordinate is output from all cells in the cell array 10. For this one row of data, data corresponding to an X coordinate selected by a multiplexer 12 according to the value of the X decoder 22 is output to an output buffer 14. In this way, the detection signal associated with each cell in the cell array 10 with the matrix structure is read.

Figure 30:
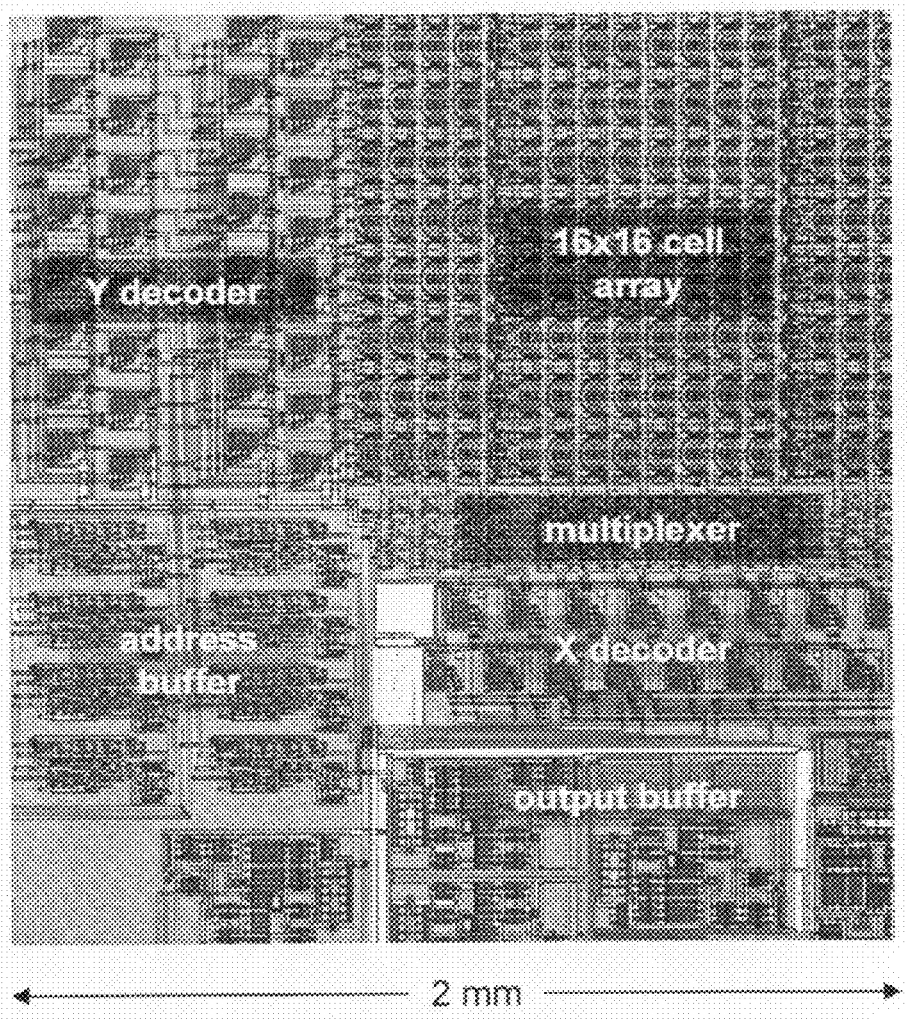
FIG. 30 is a diagram illustrating a pattern of an actual integrated circuit corresponding to the circuit shown in FIG. 29.

FIG. 30 illustrates an integrated circuit in which the circuit configuration shown in FIG. 29 is implemented.

In the present embodiment, by way of example, DNA is detected by the chip. Note that the chip according to the present embodiment can also be used to detect a biomolecule of protein, a cell, or the like. The range in which charge can be detected is limited to a region in close proximity to the gate, and more specifically, to a range of the Debye shielding length of Guoy-Chapman layer. Therefore, if a vertical gate such as that in a FINFET or a SGT (Surrounding Gate Transistor) is provided, it is possible to vertically fix a DNA molecule on a side wall. This makes it possible to detect a long molecule. Alternatively, the extension gate electrode may be formed in a double-layer structure. More specifically, the double-layer structure may include aluminum and gold, and the gold may be subjected to a fine patterning process so as to have a fine structure whose side wall can be used to fix thiolated DNA.

A heat source and a thermometer may be provided in each cell to separately control the temperature of each cell. This makes it possible to detect perfect/imperfect binding at temperatures close to the melting temperature. This allows higher accuracy in detection. This method may be combined with another method such as that using porous silicon as a heat insulator between cells.

In the first embodiment of the invention, the cell including an ISFET with a size of 100 μm×100 μm and an embedded control circuit has a size of 160 μm×140 μm, and the size of a chip including a 16×16 cell array, a peripheral circuit, and input/output pads is 4 mm×4 mm. The total consumption power of the chip is 150 mW when the power supply voltages are 3 V and −1.3 V. By reducing the cell size, it is possible to reduce the chip size, and thus it is possible to realize a high-accuracy charge detection sensor at low cost. In the second embodiment, the charge detection transistor having the gate electrode is used. This makes it possible to compensate for the variation in the threshold value or initial charge. By differentially amplifying the detection voltage, it is possible to achieve a charge detection sensor with further higher accuracy.

Another embodiment provides a chip capable of simultaneously detecting one million different charges using one million cells, wherein the chip size is 4 mm×4 mm and the consumption power is 100 mW. It is apparent that NMOSFETs and PMOSFETs in the embodiments described above may be exchanged.

INDUSTRIAL APPLICABILITY

The present invention can be used to identify DNA or detect other biomolecules or bio substances. More generally, the present invention can be applied to a detection apparatus capable of detecting a charge distribution or a substance distribution corresponding to the charge distribution.

The invention claimed is:

1. A substance detection apparatus configured to identify a substance by measuring an amount of charge of the substance in contact with a gate of a charge detection field effect transistor, comprising:
   cells arranged in the form of a matrix array, each cell including
      a charge detection field effect transistor; and
      a control circuit including a CMOS current mirror circuit configured to control the charge detection field effect transistor such that a voltage between a gate and source and a voltage between a gate and a drain of the charge detection field effect transistor are maintained constant.

2. The substance detection apparatus according to claim 1, wherein the control circuit includes a first current mirror circuit using PMOSFETs, a second current mirror circuit using NMOSFETs, and a current source, the first current mirror circuit and the second current mirror circuit being connected in series, the current source being adapted to supply a constant current to the series connection of the current mirror circuits, the charge detection field effect transistor being inserted in one of current paths, at least one selected from the group consisting of a first resistor, a first transistor and a first diode being inserted in the other one of the current paths.

3. The substance detection apparatus according to claim 2, wherein the first current mirror circuit includes cascode-connected PMOSFETs, and the second current mirror circuit includes cascode-connected NMOSFETs.

4. The substance detection apparatus according to claim 3, wherein the first current mirror circuit and the second current mirror circuit are connected to each other via at least one selected from the group consisting of a second resistor, a second transistor and a second diode, and at least one selected from the group consisting of a third resistor, a third transistor and a third diode, inserted in respective current paths.

5. The substance detection apparatus according to claim 2, wherein the current source is a circuit configured in the form of a current mirror circuit including at least one selected from the group consisting of a fourth resistor, a fourth transistor and a fourth diode functioning as a load thereby to supply a constant current.

6. The substance detection apparatus according to claim 5, wherein the first resistor, the second resistor, the third resistor, and the fourth resistor, or the first transistor, the second transistor, the third transistor, and the fourth transistor, or the first diode, the second diode, the third diode, and the fourth diode are formed of the same material.

7. The substance detection apparatus according to claim 1, wherein each cell includes a reference field effect transistor and a reference control circuit, the reference field effect transistor having the same structure as that of the charge detection field effect transistor, the reference control circuit being adapted to supply a current to the reference field effect transistor, the reference control circuit having the same configuration as that of the control circuit adapted to control the charge detection field effect transistor, and
   each cell includes a first differential amplifier adapted to input an output signal depending on an operating state of the charge detection field effect transistor and an output signal depending on an operating state of the reference field effect transistor and amplifies the difference between the two output signals.

8. The substance detection apparatus according to claim 2, wherein each cell includes a reference field effect transistor and a reference control circuit, the reference field effect transistor having the same. structure as that of the charge detection field effect transistor, the reference control circuit being adapted to supply a current to the reference field effect transistor, the reference control circuit having the same configuration as that of the control circuit adapted to control the charge detection field effect transistor, and
   each cell includes a first differential amplifier adapted to input an output signal depending on an operating state of the charge detection field effect transistor and an output signal depending on an operating state of the reference field effect transistor and amplifies the difference between the two output signals.

9. The substance detection apparatus according to claim 3, wherein each cell includes a reference field effect transistor and a reference control circuit, the reference field effect transistor having the same structure as that of the charge detection field effect transistor, the reference control circuit being adapted to supply a current to the reference field effect transistor, the reference control circuit having the same configuration as that of the control circuit adapted to control the charge detection field effect transistor, and
   each cell includes a first differential amplifier adapted to input an output signal depending on an operating state of the charge detection field effect transistor and an output signal depending on an operating state of the reference field effect transistor and amplifies the difference between the two output signals.

10. The substance detection apparatus according to claim 4, wherein each cell includes a reference field effect transistor and a reference control circuit, the reference field effect transistor having the same structure as that of the charge detection field effect transistor, the reference control circuit being adapted to supply a current to the reference field effect transistor, the reference control circuit having the same configuration as that of the control circuit adapted to control the charge detection field effect transistor, and
   each cell includes a first differential amplifier adapted to input an output signal depending on an operating state of the charge detection field effect transistor and an output signal depending on an operating state of the reference field effect transistor and amplifies the difference between the two output signals.

11. The substance detection apparatus according to claim 1, further comprising
   reference field effect transistors and reference control circuits provided for respective rows of the matrix array of cells, the reference field effect transistors and the reference control circuits being disposed in a peripheral part of an area in which the matrix array of cells is disposed, the reference field effect transistors having the same structure as that of the charge detection field effect transistors, the reference control circuits being adapted to supply currents to the corresponding reference field effect transistors, the reference control circuits having the same configuration as that of the control circuit adapted to control the charge detection field effect transistors, and
   second differential amplifiers provided for the respective rows and each adapted to input an output signal depending on an operating state of the corresponding charge detection field effect transistor and an output signal depending on an operating state of the corresponding reference field effect transistor and amplifies the difference between the two output signals.

12. The substance detection apparatus according to claim 2, further comprising
- reference field effect transistors and reference control circuits provided for respective rows of the matrix array of cells, the reference field effect transistors and the reference control circuits being disposed in a peripheral part of an area in which the matrix array of cells is disposed, the reference field effect transistors having the same structure as that of the charge detection field effect transistors, the reference control circuits being adapted to supply currents to the corresponding reference field effect transistors, the reference control circuits having the same configuration as that of the control circuit adapted to control the charge detection field effect transistors, and
- second differential amplifiers provided for the respective rows and each adapted to input an output signal depending on an operating state of the corresponding charge detection field effect transistor and an output signal depending on an operating state of the corresponding reference field effect transistor and amplifies the difference between the two output signals.

13. The substance detection apparatus according to claim 3, further comprising
- reference field effect transistors and reference control circuits provided for respective rows of the matrix array of cells, the reference field effect transistors and the reference control circuits being disposed in a peripheral part of an area in which the matrix array of cells is disposed, the reference field effect transistors having the same structure as that of the charge detection field effect transistors, the reference control circuits being adapted to supply currents to the corresponding reference field effect transistors, the reference control circuits having the same configuration as that of the control circuit adapted to control the charge detection field effect transistors, and
- second differential amplifiers provided for the respective rows and each adapted to input an output signal depending on an operating state of the corresponding charge detection field effect transistor and an output signal depending on an operating state of the corresponding reference field effect transistor and amplifies the difference between the two output signals.

14. The substance detection apparatus according to claim 4, further comprising
- reference field effect transistors and reference control circuits provided for respective rows of the matrix array of cells, the reference field effect transistors and the reference control circuits being disposed in a peripheral part of an area in which the matrix array of cells is disposed, the reference field effect transistors having the same structure as that of the charge detection field effect transistors, the reference control circuits being adapted to supply currents to the corresponding reference field effect transistors, the reference control circuits having the same configuration as that of the control circuit adapted to control the charge detection field effect transistors, and
- second differential amplifiers provided for the respective rows and each adapted to input an output signal depending on an operating state of the corresponding charge detection field effect transistor and an output signal depending on an operating state of the corresponding reference field effect transistor and amplifies the difference between the two output signals.

15. The substance detection apparatus according to claim 1, wherein each cell includes
- an output transistor for inputting the output signal of the charge detection field effect transistor and a pass gate transistor connected to the output transistor and adapted to pass or cut off the output of the output transistor depending on an external selection signal thereby outputting the output signal to the outside of the cell, and
- a signal line adapted to transmit the output signal from the pass gate transistor to a peripheral part of the area of the matrix array of cells.

16. The substance detection apparatus according to claim 15, further comprising
- a third differential amplifier disposed in a peripheral part of the area of the matrix array of cells and adapted to input the output signal from the signal line to one input terminal of the third differential amplifier,
- a resistor or a transistor connected between two input terminals of the third differential amplifier,
- a feedback line connecting the other input terminal of the third differential amplifier to each cell, and
- a feedback transistor provided in each cell and adapted to pass or cut off a signal depending on the selection signal thereby feeding back the fed-back output signal to a common potential via the feedback line.

17. The substance detection apparatus according to claim 1, wherein each charge detection field effect transistor has a gate electrode on an insulating film.

18. The substance detection apparatus according to claim 17, further comprising a charging transistor adapted to supply or cut off a bias voltage to the gate electrode.

19. The substance detection apparatus according to claim 7, wherein
- the reference field effect transistor in each cell has a gate electrode on an insulating film,
- each cell includes a first charging transistor adapted to supply or cut off a bias voltage to the gate electrode according to an external charge control signal,
- the charge detection field effect transistor in each cell has a gate electrode on an insulating film, and
- each cell includes a fourth differential amplifier and a second charging transistor, the fourth differential amplifier being adapted to input an output signal depending on an operating state of the corresponding charge detection field effect transistor and an output signal depending on an operating state of the corresponding reference field effect transistor and amplifies the difference between the two output signals, the second charging transistor being a transistor adapted to supply or cut off a bias voltage in accordance with the charge control signal so as to apply the output of the fourth differential amplifier to the gate electrode of the charge detection field effect transistor.

20. The substance detection apparatus according to claim 11, wherein
- each reference field effect transistor has a gate electrode on an insulating film, a first charging transistor is provided for supplying or cutting off a bias voltage to the gate electrode according to an external charge control signal,
- the charge detection field effect transistor in each cell has a gate electrode on an insulating film, and
- a second charging transistor is provided for applying, to the gate electrode of the charge detection field effect transistor, an amplified difference voltage between an output signal depending on an operating state of the charge detection field effect transistor and an output signal depending on an operating state of the reference field effect transistor thereby supplying or cutting off a bias voltage according to the charge control signal.

21. The substance detection apparatus according to claim 17, wherein the gate electrode of the charge detection field effect transistor is an extension gate electrode extending immediately over the charge detection field effect transistor and the control circuit.

22. The substance detection apparatus according to claim 19, wherein the gate electrode of the reference field effect transistor is an extension gate electrode extending immediately over the reference field effect transistor and the control circuit.

23. The substance detection apparatus according to claim 1, wherein a power supply voltage supplied to each cell is within the range of 3 V to −1.3 V.

24. The substance detection apparatus according to claim 1, further comprising a word line adapted to select one row of the matrix array of cells and a bit line adapted to transmit a signal from a cell in each column.

25. The substance detection apparatus according to claim 20, further comprising a fifth transistor and a sixth transistor adapted to apply voltages corresponding to voltages of gate electrodes of the reference field effect transistor and the charge detection field effect transistor to terminals, which are not connected to the gates of the reference field effect transistor and the charge detection field effect transistor, of the first charging transistor and the second charging transistor when the first charging transistor and the second charging transistor are in OFF states so that the source-drain voltage becomes zero for these first charging transistor and second charging transistor in the OFF states.

26. The substance detection apparatus according to claim 25, further comprising a seventh transistor and an eighth transistor, the seventh transistor being disposed between the gate electrode of the reference field effect transistor and the fifth transistor, the seventh transistor being adapted to absorb a charge of a channel of the first charging transistor when the first charging transistor is in an OFF state, the eighth transistor being disposed between the gate electrode of the charge detection field effect transistor and the sixth transistor, the eighth transistor being adapted to absorb a charge of a channel of the second charging transistor when the second charging transistor is in an OFF state.

27. The substance detection apparatus according to claim 1, further comprising a second output circuit adapted to output, as an output signal, a gate potential of the charge detection field effect transistor.

28. The substance detection apparatus according to claim 7, further comprising a first output circuit adapted to output, as an output signal, a gate potential of the reference field effect transistor.

29. The substance detection apparatus according to claim 27, further comprising a second startup circuit adapted to be maintained in the operating state when the gate potential of the charge detection field effect transistor is low.

30. The substance detection apparatus according to claim 28, further comprising a first startup circuit adapted to be maintained in the operating state when the gate potential of the reference field effect transistor is low.

31. The substance detection apparatus according to claim 1, further comprising a bias circuit adapted to supply a bias voltage to a transistor in each cell, the bias circuit including a current mirror circuit adapted to control currents such that a reference current flowing through a charge detection transistor is equal for adjacent cells, the bias circuit also including a current mirror circuit adapted to control currents such that the reference current is equal to a reference current that is input to the current mirror circuit.

32. The substance detection apparatus according to claim 31, wherein the reference current is controlled to have a large value for a cell being measured and to have a small value for a cell being not measured.

33. The substance detection apparatus according to claim 1, wherein the substance detection apparatus is an apparatus adapted to detect one of DNA, a biomolecule, a biocell group, and a bio substance.

34. The substance detection apparatus according to claim 20, wherein the gate electrode of the reference field effect transistor is an extension gate electrode extending immediately over the reference field effect transistor and the control circuit.

35. The substance detection apparatus according to claim 19, further comprising a fifth transistor and a sixth transistor adapted to apply voltages corresponding to voltages of gate electrodes of the reference field effect transistor and the charge detection field effect transistor to terminals, which are not connected to the gates of the reference field effect transistor and the charge detection field effect transistor, of the first charging transistor and the second charging transistor when the first charging transistor and the second charging transistor are in OFF states so that the source-drain voltage becomes zero for these first charging transistor and second charging transistor in the OFF states.

36. The substance detection apparatus according to claim 35, further comprising a seventh transistor and an eighth transistor, the seventh transistor being disposed between the gate electrode of the reference field effect transistor and the fifth transistor, the seventh transistor being adapted to absorb a charge of a channel of the first charging transistor when the first charging transistor is in an OFF state, the eighth transistor being disposed between the gate electrode of the charge detection field effect transistor and the sixth transistor, the eighth transistor being adapted to absorb a charge of a channel of the second charging transistor when the second charging transistor is in an OFF state.

\* \* \* \* \*